US008603168B2

(12) United States Patent
Gordon et al.

(10) Patent No.: US 8,603,168 B2
(45) Date of Patent: Dec. 10, 2013

(54) ARTIFICIAL FUNCTIONAL SPINAL UNIT SYSTEM AND METHOD FOR USE

(75) Inventors: Charles R. Gordon, Tyler, TX (US);
Corey T. Harbold, Tyler, TX (US);
Heather S. Hanson, San Antonio, TX (US); Erik J. Wagner, Austin, TX (US)

(73) Assignee: Flexuspine, Inc., Pittsburgh, PA (US)

( * ) Notice: Subject to any disclaimer, the term of this patent is extended or adjusted under 35 U.S.C. 154(b) by 0 days.

(21) Appl. No.: 11/371,376

(22) Filed: Mar. 8, 2006

(65) Prior Publication Data
US 2007/0270972 A1    Nov. 22, 2007

Related U.S. Application Data

(63) Continuation-in-part of application No. 10/634,950, filed on Aug. 5, 2003, now Pat. No. 7,204,853.

(51) Int. Cl.
A61F 2/44           (2006.01)
(52) U.S. Cl.
USPC ............. 623/17.14; 623/17.15; 606/254; 606/260
(58) Field of Classification Search
USPC ........... 606/61, 300, 259, 260, 261, 262, 263, 606/264, 265, 266, 267, 269, 270, 271, 272, 606/273, 274, 275, 276, 277, 278, 279, 246, 606/247, 248, 249, 250, 251, 252, 253, 254, 606/255, 256, 257, 258; 623/17.11–17.16
See application file for complete search history.

(56) References Cited

U.S. PATENT DOCUMENTS

| 3,848,601 | A | 11/1974 | Ma et al. |
| 3,867,728 | A | 2/1975 | Stubstad et al. |
| 4,309,777 | A | 1/1982 | Patil |
| 4,349,921 | A | 9/1982 | Kuntz |
| 4,611,581 | A | 9/1986 | Steffee |
| 4,657,550 | A | 4/1987 | Daher |
| 4,696,290 | A | 9/1987 | Steffee |
| 4,743,260 | A | 5/1988 | Burton |
| 4,759,766 | A | 7/1988 | Buettner-Janz et al. |
| 4,759,769 | A | 7/1988 | Hedman et al. |
| 4,772,287 | A | 9/1988 | Ray et al. |

(Continued)

FOREIGN PATENT DOCUMENTS

| FR | 2716616 | 9/1995 |
| FR | 2718946 | 10/1995 |

(Continued)

OTHER PUBLICATIONS

Co-pending U.S. Appl. No. 11/655,737 entitled "Dynamic Interbody Device" to Landry et al. filed Jan. 19, 2007.

(Continued)

Primary Examiner — Jan Christopher Merene
(74) Attorney, Agent, or Firm — Meyertons, Hood, Kivlin, Kowert & Goetzel, P.C.; Eric B. Meyertons

(57) ABSTRACT

A stabilization system for a human spine is provided comprising at least one dynamic interbody device and at least one dynamic posterior stabilization system. In some embodiments the stabilization system comprises a pair of dynamic interbody devices and a pair of dynamic posterior stabilization systems. In some embodiments, a bridge may couple a dynamic interbody device to a dynamic posterior stabilization system.

30 Claims, 12 Drawing Sheets

(56) References Cited

U.S. PATENT DOCUMENTS

| | | |
|---|---|---|
| 4,854,311 A | 8/1989 | Steffee |
| 4,863,476 A | 9/1989 | Shepperd |
| 4,863,477 A | 9/1989 | Monson |
| 4,907,577 A | 3/1990 | Wu |
| 4,911,718 A | 3/1990 | Lee et al. |
| 4,932,975 A | 6/1990 | Main et al. |
| 4,946,378 A | 8/1990 | Hirayama et al. |
| 4,946,458 A | 8/1990 | Harms et al. |
| 5,042,982 A | 8/1991 | Harms et al. |
| 5,047,055 A | 9/1991 | Bao et al. |
| 5,059,194 A | 10/1991 | Michelson |
| 5,071,437 A | 12/1991 | Steffee |
| 5,092,867 A | 3/1992 | Harms et al. |
| 5,108,438 A | 4/1992 | Stone |
| 5,123,926 A | 6/1992 | Pisharodi |
| 5,171,278 A | 12/1992 | Pisharodi |
| 5,171,281 A | 12/1992 | Parsons et al. |
| 5,180,393 A | 1/1993 | Commarmond |
| 5,192,326 A | 3/1993 | Bao et al. |
| 5,196,013 A | 3/1993 | Harms et al. |
| 5,207,678 A | 5/1993 | Harms et al. |
| 5,246,458 A | 9/1993 | Graham |
| 5,258,031 A | 11/1993 | Salib et al. |
| 5,261,909 A | 11/1993 | Sutterlin et al. |
| 5,306,307 A | 4/1994 | Senter et al. |
| 5,306,309 A | 4/1994 | Wagner et al. |
| 5,314,477 A | 5/1994 | Marnay |
| 5,320,644 A | 6/1994 | Baumgartner |
| 5,336,223 A | 8/1994 | Rogers |
| 5,370,697 A | 12/1994 | Baumgartner |
| 5,375,823 A * | 12/1994 | Navas .................. 623/17.15 |
| 5,397,364 A | 3/1995 | Kozak et al. |
| 5,401,269 A | 3/1995 | Buttner-Janz et al. |
| 5,403,315 A | 4/1995 | Ashman |
| 5,415,661 A | 5/1995 | Holmes |
| 5,423,816 A | 6/1995 | Lin |
| 5,425,773 A | 6/1995 | Boyd et al. |
| 5,443,467 A | 8/1995 | Biedermann et al. |
| 5,458,642 A | 10/1995 | Beer et al. |
| 5,458,643 A | 10/1995 | Oka et al. |
| 5,480,401 A | 1/1996 | Navas |
| 5,496,321 A | 3/1996 | Puno et al. |
| 5,498,263 A | 3/1996 | DiNello et al. |
| 5,514,132 A | 5/1996 | Csernatony et al. |
| 5,514,180 A | 5/1996 | Heggeness et al. |
| 5,522,899 A | 6/1996 | Michelson |
| 5,534,028 A | 7/1996 | Bao et al. |
| 5,534,029 A | 7/1996 | Shima |
| 5,534,030 A | 7/1996 | Navarro et al. |
| 5,545,165 A | 8/1996 | Biedermann et al. |
| 5,556,431 A | 9/1996 | Buttner-Janz |
| 5,562,663 A | 10/1996 | Wisnewski et al. |
| 5,562,737 A | 10/1996 | Graf |
| 5,562,738 A | 10/1996 | Boyd et al. |
| 5,571,109 A | 11/1996 | Bertagnoli |
| 5,609,635 A | 3/1997 | Michelson |
| 5,645,599 A | 7/1997 | Samani |
| 5,653,763 A | 8/1997 | Errico et al. |
| 5,665,122 A | 9/1997 | Kambin |
| 5,672,175 A | 9/1997 | Martin |
| 5,672,176 A | 9/1997 | Biedermann et al. |
| 5,674,294 A | 10/1997 | Bainville et al. |
| 5,674,296 A | 10/1997 | Bryan et al. |
| 5,676,701 A | 10/1997 | Yuan et al. |
| 5,676,702 A | 10/1997 | Ratron |
| 5,683,391 A * | 11/1997 | Boyd .................. 606/61 |
| 5,683,464 A | 11/1997 | Wagner et al. |
| 5,702,450 A | 12/1997 | Bisserie |
| 5,725,527 A | 3/1998 | Biedermann et al. |
| 5,733,284 A | 3/1998 | Martin |
| 5,741,253 A | 4/1998 | Michelson |
| 5,755,797 A | 5/1998 | Baumgartner |
| 5,776,199 A | 7/1998 | Michelson |
| 5,782,832 A | 7/1998 | Larsen et al. |
| 5,785,647 A | 7/1998 | Tompkins et al. |
| 5,797,909 A | 8/1998 | Michelson |
| 5,800,549 A | 9/1998 | Bao et al. |
| 5,800,550 A | 9/1998 | Sertich |
| 5,810,819 A | 9/1998 | Errico et al. |
| 5,824,093 A | 10/1998 | Ray et al. |
| 5,824,094 A | 10/1998 | Serhan et al. |
| 5,827,328 A | 10/1998 | Buttermann |
| 5,861,041 A | 1/1999 | Tienboon |
| 5,863,293 A | 1/1999 | Richelsoph |
| 5,863,465 A | 1/1999 | Kinlen |
| 5,865,846 A | 2/1999 | Bryan et al. |
| 5,865,848 A | 2/1999 | Baker |
| 5,888,220 A | 3/1999 | Felt et al. |
| 5,888,226 A | 3/1999 | Rogozinski |
| 5,893,889 A | 4/1999 | Harrington |
| 5,895,427 A | 4/1999 | Kuslich et al. |
| 5,895,428 A | 4/1999 | Berry |
| 5,899,941 A | 5/1999 | Nishijima et al. |
| 5,928,243 A | 7/1999 | Guyer |
| 5,935,133 A | 8/1999 | Wagner et al. |
| 5,938,663 A | 8/1999 | Petreto |
| 5,951,555 A | 9/1999 | Rehak et al. |
| 5,961,518 A | 10/1999 | Errico et al. |
| 5,961,554 A | 10/1999 | Janson et al. |
| 5,964,769 A | 10/1999 | Wagner et al. |
| 5,976,186 A | 11/1999 | Bao et al. |
| 5,980,522 A | 11/1999 | Koros et al. |
| 5,984,967 A | 11/1999 | Zdeblick et al. |
| 5,989,250 A | 11/1999 | Wagner et al. |
| 5,989,290 A | 11/1999 | Biedermann et al. |
| 5,997,539 A | 12/1999 | Errico et al. |
| 6,001,130 A | 12/1999 | Bryan et al. |
| 6,017,344 A | 1/2000 | Errico et al. |
| 6,019,792 A | 2/2000 | Cauthen |
| 6,022,376 A | 2/2000 | Assell et al. |
| 6,030,389 A | 2/2000 | Wagner et al. |
| 6,039,763 A | 3/2000 | Shelokov |
| 6,045,579 A | 4/2000 | Hochshuler et al. |
| 6,053,921 A | 4/2000 | Wagner et al. |
| 6,063,089 A | 5/2000 | Errico et al. |
| RE36,758 E | 6/2000 | Fitz |
| 6,080,193 A | 6/2000 | Hochshuler et al. |
| 6,093,205 A | 7/2000 | McLeod et al. |
| 6,096,038 A | 8/2000 | Michelson |
| 6,102,950 A | 8/2000 | Vaccaro |
| 6,106,526 A | 8/2000 | Harms et al. |
| 6,110,210 A | 8/2000 | Norton et al. |
| 6,113,637 A | 9/2000 | Gill et al. |
| 6,123,707 A | 9/2000 | Wagner et al. |
| 6,126,689 A | 10/2000 | Brett |
| 6,132,430 A | 10/2000 | Wagner et al. |
| 6,132,464 A | 10/2000 | Martin |
| 6,132,465 A | 10/2000 | Ray et al. |
| 6,136,031 A | 10/2000 | Middleton |
| 6,139,579 A | 10/2000 | Steffee et al. |
| 6,146,421 A | 11/2000 | Gordon et al. |
| 6,146,422 A | 11/2000 | Lawson |
| 6,156,067 A | 12/2000 | Bryan et al. |
| 6,162,252 A | 12/2000 | Kuras et al. |
| 6,165,218 A | 12/2000 | Husson et al. |
| 6,176,882 B1 | 1/2001 | Biedermann et al. |
| 6,179,874 B1 | 1/2001 | Cauthen |
| 6,187,048 B1 | 2/2001 | Milner et al. |
| 6,200,348 B1 | 3/2001 | Biedermann et al. |
| 6,206,924 B1 | 3/2001 | Timm |
| 6,214,049 B1 | 4/2001 | Gayer et al. |
| 6,214,050 B1 | 4/2001 | Huene |
| 6,217,579 B1 | 4/2001 | Koros |
| 6,228,118 B1 | 5/2001 | Gordon |
| 6,231,609 B1 | 5/2001 | Mehdizadeh |
| 6,241,730 B1 * | 6/2001 | Alby .................. 606/256 |
| 6,264,656 B1 | 7/2001 | Michelson |
| 6,290,724 B1 | 9/2001 | Marino |
| 6,296,664 B1 | 10/2001 | Middleton |
| 6,315,797 B1 | 11/2001 | Middleton |
| 6,331,179 B1 | 12/2001 | Freid et al. |
| 6,348,071 B1 | 2/2002 | Steffee et al. |
| RE37,665 E | 4/2002 | Ralph et al. |
| 6,368,350 B1 | 4/2002 | Erickson et al. |

(56) References Cited

U.S. PATENT DOCUMENTS

| | | |
|---|---|---|
| 6,368,351 B1 | 4/2002 | Glenn et al. |
| 6,371,990 B1 | 4/2002 | Ferree |
| 6,375,682 B1 | 4/2002 | Fleischmann et al. |
| 6,375,683 B1 | 4/2002 | Crozet et al. |
| 6,391,030 B1 | 5/2002 | Wagner et al. |
| 6,395,032 B1 | 5/2002 | Gauchet |
| 6,395,034 B1 | 5/2002 | Suddaby |
| 6,402,784 B1 | 6/2002 | Wardlaw |
| 6,402,785 B1 | 6/2002 | Zdeblick et al. |
| 6,409,766 B1 | 6/2002 | Brett |
| 6,413,259 B1 | 7/2002 | Lyons et al. |
| 6,416,515 B1 | 7/2002 | Wagner et al. |
| 6,419,703 B1 | 7/2002 | Fallin et al. |
| 6,419,704 B1 | 7/2002 | Ferree |
| 6,436,140 B1 | 8/2002 | Liu et al. |
| 6,440,168 B1 | 8/2002 | Cauthen |
| 6,442,814 B1 | 9/2002 | Landry et al. |
| 6,443,990 B1 | 9/2002 | Aebi et al. |
| 6,447,512 B1 | 9/2002 | Landry et al. |
| 6,447,544 B1 | 9/2002 | Michelson |
| 6,451,021 B1 | 9/2002 | Ralph et al. |
| 6,454,769 B2 | 9/2002 | Wagner et al. |
| 6,454,806 B1 | 9/2002 | Cohen et al. |
| 6,454,807 B1 | 9/2002 | Jackson |
| 6,478,822 B1 | 11/2002 | Leroux et al. |
| 6,478,823 B1 | 11/2002 | Michelson |
| 6,482,207 B1 | 11/2002 | Errico |
| 6,482,234 B1 | 11/2002 | Weber et al. |
| 6,488,710 B2 | 12/2002 | Besselink |
| 6,500,205 B1 | 12/2002 | Michelson |
| 6,520,996 B1 | 2/2003 | Manasas et al. |
| 6,524,312 B2 | 2/2003 | Landry et al. |
| 6,533,817 B1 | 3/2003 | Norton et al. |
| 6,533,818 B1 | 3/2003 | Weber et al. |
| 6,540,748 B2 | 4/2003 | Lombardo |
| 6,558,423 B1 | 5/2003 | Michelson |
| 6,562,040 B1 | 5/2003 | Wagner et al. |
| 6,562,074 B2 | 5/2003 | Gerbec et al. |
| 6,565,566 B1 | 5/2003 | Wagner et al. |
| 6,565,605 B2 | 5/2003 | Goble et al. |
| 6,569,442 B2 | 5/2003 | Gan et al. |
| 6,572,653 B1 | 6/2003 | Simonson |
| 6,576,016 B1 | 6/2003 | Hochshuler et al. |
| 6,579,318 B2 | 6/2003 | Varga et al. |
| 6,579,319 B2 | 6/2003 | Goble et al. |
| 6,582,467 B1 | 6/2003 | Teitelbaum et al. |
| 6,595,992 B1 | 7/2003 | Wagner et al. |
| 6,595,998 B2 | 7/2003 | Johnson et al. |
| 6,610,091 B1 | 8/2003 | Reiley |
| 6,610,094 B2 | 8/2003 | Husson |
| 6,613,050 B1 | 9/2003 | Wagner et al. |
| 6,616,671 B2 | 9/2003 | Landry et al. |
| 6,626,904 B1 | 9/2003 | Jammet et al. |
| 6,626,905 B1 | 9/2003 | Schmiel et al. |
| 6,635,062 B2 | 10/2003 | Ray et al. |
| 6,641,614 B1 | 11/2003 | Wagner et al. |
| 6,648,893 B2 | 11/2003 | Dudasik |
| 6,648,915 B2 | 11/2003 | Sazy |
| 6,648,917 B2 | 11/2003 | Gerbec et al. |
| 6,666,870 B2 | 12/2003 | Dixon |
| 6,666,891 B2 | 12/2003 | Boehm et al. |
| 6,679,915 B1 | 1/2004 | Cauthen |
| 6,682,533 B1 | 1/2004 | Dinsdale et al. |
| 6,685,742 B1 | 2/2004 | Jackson |
| 6,692,495 B1 | 2/2004 | Zacouto |
| 6,706,070 B1 | 3/2004 | Wagner et al. |
| 6,712,819 B2 | 3/2004 | Zucherman et al. |
| 6,716,247 B2 | 4/2004 | Michelson |
| 6,719,796 B2 | 4/2004 | Cohen et al. |
| 6,733,531 B1 * | 5/2004 | Trieu .................. 623/17.11 |
| 6,736,850 B2 | 5/2004 | Davis |
| 6,743,257 B2 | 6/2004 | Castro |
| 6,758,861 B2 | 7/2004 | Ralph et al. |
| 6,773,460 B2 | 8/2004 | Jackson |
| 6,802,844 B2 | 10/2004 | Ferree |
| 6,811,567 B2 | 11/2004 | Reiley |
| 6,821,298 B1 | 11/2004 | Jackson |
| 6,852,129 B2 | 2/2005 | Gerbec et al. |
| 6,863,673 B2 | 3/2005 | Gerbec et al. |
| D505,205 S | 5/2005 | Freid |
| 6,893,464 B2 | 5/2005 | Kiester |
| 6,902,580 B2 | 6/2005 | Fallin et al. |
| 6,928,284 B2 | 8/2005 | Palat et al. |
| 6,936,070 B1 | 8/2005 | Muhanna |
| 6,953,477 B2 | 10/2005 | Berry |
| 6,962,606 B2 | 11/2005 | Michelson |
| 6,964,664 B2 | 11/2005 | Freid et al. |
| 6,966,929 B2 | 11/2005 | Mitchell |
| 6,966,930 B2 | 11/2005 | Arnin et al. |
| 6,974,478 B2 | 12/2005 | Reiley et al. |
| 6,981,989 B1 | 1/2006 | Fleischmann et al. |
| 6,991,632 B2 | 1/2006 | Ritland |
| 6,994,727 B2 | 2/2006 | Khandkar et al. |
| 6,997,929 B2 | 2/2006 | Manzi et al. |
| 7,011,685 B2 | 3/2006 | Arnin et al. |
| 7,018,415 B1 | 3/2006 | McKay |
| 7,029,475 B2 | 4/2006 | Panjabi |
| 7,083,622 B2 | 8/2006 | Simonson |
| 7,083,649 B2 | 8/2006 | Zucherman et al. |
| 7,090,698 B2 | 8/2006 | Goble et al. |
| 7,101,398 B2 | 9/2006 | Dooris et al. |
| 7,118,579 B2 | 10/2006 | Michelson |
| 7,118,580 B1 | 10/2006 | Beyersdorff et al. |
| 7,128,760 B2 | 10/2006 | Michelson |
| 7,147,664 B2 | 12/2006 | Louis et al. |
| 7,153,310 B2 | 12/2006 | Ralph et al. |
| 7,204,853 B2 | 4/2007 | Gordon et al. |
| 7,273,496 B2 | 9/2007 | Mitchell |
| 7,291,150 B2 * | 11/2007 | Graf .................. 606/86 A |
| 7,291,173 B2 | 11/2007 | Richelsoph et al. |
| 7,311,713 B2 | 12/2007 | Johnson et al. |
| 7,316,714 B2 | 1/2008 | Gordon et al. |
| 7,318,839 B2 | 1/2008 | Malberg et al. |
| 7,320,707 B2 | 1/2008 | Zucherman |
| 7,326,250 B2 | 2/2008 | Beaurain et al. |
| 7,338,525 B2 | 3/2008 | Ferree |
| 7,338,527 B2 | 3/2008 | Blatt et al. |
| 7,364,589 B2 | 4/2008 | Eisermann |
| 7,473,276 B2 | 1/2009 | Aebi et al. |
| 7,476,238 B2 | 1/2009 | Panjabi |
| 7,485,146 B1 | 2/2009 | Crook et al. |
| 7,517,359 B2 | 4/2009 | Drewry et al. |
| 7,547,309 B2 | 6/2009 | Bertagnoli et al. |
| 7,550,009 B2 | 6/2009 | Arnin et al. |
| 7,556,651 B2 | 7/2009 | Humphreys et al. |
| 7,615,068 B2 | 11/2009 | Timm et al. |
| 7,635,379 B2 | 12/2009 | Callahan et al. |
| 7,682,396 B2 | 3/2010 | Beaurain et al. |
| 7,699,875 B2 | 4/2010 | Timm et al. |
| 7,708,778 B2 | 5/2010 | Gordon et al. |
| 7,713,287 B2 | 5/2010 | Timm et al. |
| 7,713,288 B2 | 5/2010 | Timm et al. |
| 7,753,958 B2 | 7/2010 | Gordon et al. |
| 7,771,479 B2 | 8/2010 | Humphreys et al. |
| 7,785,351 B2 | 8/2010 | Gordon et al. |
| 7,794,480 B2 | 9/2010 | Gordon et al. |
| 7,799,082 B2 | 9/2010 | Gordon et al. |
| 7,811,309 B2 | 10/2010 | Timm et al. |
| 7,909,869 B2 | 3/2011 | Gordon et al. |
| 7,909,877 B2 | 3/2011 | Krueger et al. |
| 7,931,675 B2 | 4/2011 | Panjabi et al. |
| 7,942,905 B2 | 5/2011 | Lim et al. |
| 7,951,170 B2 | 5/2011 | Jackson |
| 7,959,677 B2 | 6/2011 | Landry et al. |
| 8,043,379 B2 | 10/2011 | Moumene et al. |
| 8,052,723 B2 | 11/2011 | Gordon et al. |
| 8,062,375 B2 | 11/2011 | Glerum et al. |
| 8,105,382 B2 | 1/2012 | Olmos et al. |
| 8,118,869 B2 | 2/2012 | Gordon et al. |
| 8,118,870 B2 | 2/2012 | Gordon et al. |
| 8,118,871 B2 | 2/2012 | Gordon et al. |
| 8,123,810 B2 | 2/2012 | Gordon et al. |
| 8,157,844 B2 | 4/2012 | Gimbel et al. |
| 8,172,903 B2 | 5/2012 | Gordon et al. |

(56) References Cited

U.S. PATENT DOCUMENTS

| | | |
|---|---|---|
| 8,182,514 B2 | 5/2012 | Gimbel et al. |
| 8,187,330 B2 | 5/2012 | Gimbel et al. |
| 8,257,440 B2 | 9/2012 | Gordon et al. |
| 8,267,965 B2 | 9/2012 | Gimbel et al. |
| 8,377,098 B2 | 2/2013 | Landry et al. |
| 8,388,687 B2 | 3/2013 | Gimbel et al. |
| 2001/0020476 A1 | 9/2001 | Gan et al. |
| 2001/0032020 A1 | 10/2001 | Besselink |
| 2002/0040243 A1 | 4/2002 | Attali et al. |
| 2002/0045945 A1 | 4/2002 | Liu et al. |
| 2002/0065557 A1 | 5/2002 | Goble et al. |
| 2002/0068977 A1 | 6/2002 | Jackson |
| 2002/0072801 A1 | 6/2002 | Michelson |
| 2002/0082701 A1 | 6/2002 | Zdeblick et al. |
| 2002/0091390 A1 | 7/2002 | Michelson |
| 2002/0095154 A1 | 7/2002 | Atkinson et al. |
| 2002/0123806 A1 | 9/2002 | Reiley |
| 2002/0128659 A1 | 9/2002 | Michelson |
| 2002/0128714 A1 | 9/2002 | Manasas et al. |
| 2002/0130112 A1 | 9/2002 | Manasas et al. |
| 2002/0138077 A1 | 9/2002 | Ferree |
| 2002/0143401 A1 | 10/2002 | Michelson |
| 2003/0028250 A1 | 2/2003 | Reiley et al. |
| 2003/0040802 A1 | 2/2003 | Errico |
| 2003/0069643 A1 | 4/2003 | Ralph et al. |
| 2003/0074063 A1 | 4/2003 | Gerbec et al. |
| 2003/0074066 A1 | 4/2003 | Errico et al. |
| 2003/0074067 A1 | 4/2003 | Errico et al. |
| 2003/0074068 A1 | 4/2003 | Errico et al. |
| 2003/0074069 A1 | 4/2003 | Errico et al. |
| 2003/0074070 A1 | 4/2003 | Errico et al. |
| 2003/0074071 A1 | 4/2003 | Errico et al. |
| 2003/0074072 A1 | 4/2003 | Errico et al. |
| 2003/0074073 A1 | 4/2003 | Errico et al. |
| 2003/0074074 A1 | 4/2003 | Errico et al. |
| 2003/0135275 A1 | 7/2003 | Garcia et al. |
| 2003/0135277 A1 | 7/2003 | Bryan et al. |
| 2003/0139812 A1 | 7/2003 | Garcia et al. |
| 2003/0149483 A1 | 8/2003 | Michelson |
| 2003/0176923 A1 | 9/2003 | Keller et al. |
| 2003/0191470 A1 | 10/2003 | Ritland |
| 2003/0204259 A1 | 10/2003 | Goble et al. |
| 2003/0204260 A1* | 10/2003 | Ferree ..................... 623/17.11 |
| 2003/0220643 A1 | 11/2003 | Ferree |
| 2003/0225409 A1 | 12/2003 | Freid et al. |
| 2003/0233145 A1 | 12/2003 | Landry et al. |
| 2004/0006391 A1 | 1/2004 | Reiley |
| 2004/0019353 A1 | 1/2004 | Freid et al. |
| 2004/0030387 A1 | 2/2004 | Landry et al. |
| 2004/0030389 A1 | 2/2004 | Ferree |
| 2004/0039448 A1 | 2/2004 | Pisharodi |
| 2004/0044411 A1 | 3/2004 | Suddaby |
| 2004/0049190 A1 | 3/2004 | Biedermann et al. |
| 2004/0049271 A1 | 3/2004 | Biedermann et al. |
| 2004/0049272 A1 | 3/2004 | Reiley |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049280 A1 | 3/2004 | Cauthen |
| 2004/0049281 A1 | 3/2004 | Reiley |
| 2004/0087947 A1 | 5/2004 | Lim et al. |
| 2004/0093083 A1 | 5/2004 | Branch et al. |
| 2004/0102774 A1 | 5/2004 | Trieu |
| 2004/0106997 A1 | 6/2004 | Lieberson |
| 2004/0117020 A1 | 6/2004 | Frey et al. |
| 2004/0127989 A1 | 7/2004 | Dooris et al. |
| 2004/0133278 A1 | 7/2004 | Marino et al. |
| 2004/0133281 A1 | 7/2004 | Khandkar et al. |
| 2004/0138662 A1 | 7/2004 | Landry et al. |
| 2004/0138749 A1 | 7/2004 | Zucherman |
| 2004/0143265 A1 | 7/2004 | Landry et al. |
| 2004/0143332 A1 | 7/2004 | Krueger et al. |
| 2004/0147928 A1 | 7/2004 | Landry et al. |
| 2004/0153065 A1 | 8/2004 | Lim |
| 2004/0167626 A1 | 8/2004 | Geremakis et al. |
| 2004/0181223 A1 | 9/2004 | Ritland |
| 2004/0181284 A1 | 9/2004 | Simonson |
| 2004/0220567 A1 | 11/2004 | Eisermann et al. |
| 2004/0236327 A1 | 11/2004 | Paul et al. |
| 2004/0236329 A1 | 11/2004 | Panjabi |
| 2004/0243240 A1 | 12/2004 | Beaurain et al. |
| 2004/0254643 A1 | 12/2004 | Jackson |
| 2004/0254644 A1 | 12/2004 | Taylor |
| 2004/0267364 A1 | 12/2004 | Carli et al. |
| 2004/0267369 A1 | 12/2004 | Lyons et al. |
| 2005/0010295 A1 | 1/2005 | Michelson |
| 2005/0015146 A1 | 1/2005 | Louis et al. |
| 2005/0015149 A1 | 1/2005 | Michelson |
| 2005/0021144 A1 | 1/2005 | Malberg et al. |
| 2005/0027361 A1 | 2/2005 | Reiley |
| 2005/0033431 A1 | 2/2005 | Gordon et al. |
| 2005/0033432 A1 | 2/2005 | Gordon et al. |
| 2005/0033437 A1 | 2/2005 | Bao et al. |
| 2005/0033439 A1 | 2/2005 | Gordon et al. |
| 2005/0060034 A1 | 3/2005 | Berry |
| 2005/0085815 A1 | 4/2005 | Harms et al. |
| 2005/0107881 A1 | 5/2005 | Alleyne et al. |
| 2005/0113927 A1 | 5/2005 | Malek |
| 2005/0124991 A1 | 6/2005 | Jahng |
| 2005/0125061 A1 | 6/2005 | Zucherman et al. |
| 2005/0131406 A1 | 6/2005 | Reiley |
| 2005/0143818 A1 | 6/2005 | Yuan et al. |
| 2005/0149020 A1 | 7/2005 | Jahng |
| 2005/0149023 A1 | 7/2005 | Ritland |
| 2005/0154461 A1 | 7/2005 | Humphreys et al. |
| 2005/0154465 A1 | 7/2005 | Hodges et al. |
| 2005/0154466 A1 | 7/2005 | Humphreys et al. |
| 2005/0159818 A1 | 7/2005 | Blain |
| 2005/0171543 A1 | 8/2005 | Timm et al. |
| 2005/0171608 A1 | 8/2005 | Peterman et al. |
| 2005/0171610 A1* | 8/2005 | Humphreys et al. ....... 623/17.15 |
| 2005/0177156 A1 | 8/2005 | Timm et al. |
| 2005/0177157 A1 | 8/2005 | Jahng |
| 2005/0177164 A1 | 8/2005 | Walters et al. |
| 2005/0177166 A1 | 8/2005 | Timm et al. |
| 2005/0182401 A1 | 8/2005 | Timm et al. |
| 2005/0182409 A1 | 8/2005 | Callahan et al. |
| 2005/0203517 A1 | 9/2005 | Jahng et al. |
| 2005/0209697 A1 | 9/2005 | Paponneau et al. |
| 2005/0209698 A1 | 9/2005 | Gordon et al. |
| 2005/0222569 A1 | 10/2005 | Panjabi |
| 2005/0228500 A1 | 10/2005 | Kim et al. |
| 2005/0245930 A1 | 11/2005 | Timm et al. |
| 2005/0256578 A1 | 11/2005 | Blatt et al. |
| 2005/0273167 A1 | 12/2005 | Triplett et al. |
| 2005/0273171 A1 | 12/2005 | Gordon et al. |
| 2005/0273173 A1 | 12/2005 | Gordon et al. |
| 2005/0273174 A1 | 12/2005 | Gordon et al. |
| 2005/0273175 A1 | 12/2005 | Gordon et al. |
| 2005/0278026 A1 | 12/2005 | Gordon et al. |
| 2005/0283244 A1 | 12/2005 | Gordon et al. |
| 2005/0283245 A1 | 12/2005 | Gordon et al. |
| 2005/0283247 A1 | 12/2005 | Gordon et al. |
| 2005/0283248 A1 | 12/2005 | Gordon et al. |
| 2005/0288670 A1 | 12/2005 | Panjabi et al. |
| 2006/0009768 A1 | 1/2006 | Ritland |
| 2006/0009850 A1 | 1/2006 | Frigg et al. |
| 2006/0015100 A1 | 1/2006 | Panjabi et al. |
| 2006/0036240 A1 | 2/2006 | Colleran et al. |
| 2006/0036245 A1 | 2/2006 | Stern |
| 2006/0084986 A1 | 4/2006 | Grinberg et al. |
| 2006/0089717 A1 | 4/2006 | Krishna et al. |
| 2006/0095132 A1 | 5/2006 | Kirschman |
| 2006/0129244 A1 | 6/2006 | Ensign |
| 2006/0142759 A1 | 6/2006 | Arnin et al. |
| 2006/0149228 A1 | 7/2006 | Schlapfer et al. |
| 2006/0149229 A1 | 7/2006 | Kwak et al. |
| 2006/0149278 A1 | 7/2006 | Abdou |
| 2006/0149383 A1 | 7/2006 | Arnin et al. |
| 2006/0155377 A1 | 7/2006 | Beaurain et al. |
| 2006/0167547 A1 | 7/2006 | Suddaby |

(56) References Cited

U.S. PATENT DOCUMENTS

| | | | |
|---|---|---|---|
| 2006/0189983 A1 | 8/2006 | Fallin et al. | |
| 2006/0195114 A1 | 8/2006 | Bertagnoli | |
| 2006/0195191 A1 | 8/2006 | Sweeney et al. | |
| 2006/0195192 A1 | 8/2006 | Gordon et al. | |
| 2006/0217712 A1 | 9/2006 | Mueller et al. | |
| 2006/0229729 A1 | 10/2006 | Gordon | |
| 2006/0241642 A1 | 10/2006 | Arnin et al. | |
| 2006/0241769 A1 | 10/2006 | Gordon et al. | |
| 2006/0241770 A1 | 10/2006 | Rhoda et al. | |
| 2006/0241771 A1 | 10/2006 | Gordon et al. | |
| 2006/0247635 A1 | 11/2006 | Gordon et al. | |
| 2006/0247779 A1 | 11/2006 | Gordon et al. | |
| 2006/0260483 A1 | 11/2006 | Hartmann et al. | |
| 2006/0264937 A1 | 11/2006 | White | |
| 2006/0265068 A1 | 11/2006 | Schwab | |
| 2006/0265074 A1* | 11/2006 | Krishna et al. | 623/17.15 |
| 2007/0010886 A1 | 1/2007 | Banick | |
| 2007/0073405 A1 | 3/2007 | Verhulst et al. | |
| 2007/0073406 A1 | 3/2007 | Gordon et al. | |
| 2007/0093828 A1 | 4/2007 | Abdou | |
| 2007/0093846 A1 | 4/2007 | Frigg et al. | |
| 2007/0162137 A1 | 7/2007 | Kloss et al. | |
| 2007/0213720 A1 | 9/2007 | Gordon et al. | |
| 2007/0213821 A1 | 9/2007 | Kwak et al. | |
| 2007/0225814 A1 | 9/2007 | Atkinson | |
| 2007/0239279 A1 | 10/2007 | Francis | |
| 2007/0270838 A1 | 11/2007 | Bruneau et al. | |
| 2007/0270972 A1 | 11/2007 | Gordon et al. | |
| 2008/0015702 A1 | 1/2008 | Lakin et al. | |
| 2008/0027547 A1 | 1/2008 | Yu et al. | |
| 2008/0033562 A1 | 2/2008 | Krishna | |
| 2008/0065079 A1 | 3/2008 | Bruneau et al. | |
| 2008/0133013 A1 | 6/2008 | Duggal et al. | |
| 2008/0161853 A1 | 7/2008 | Arnold et al. | |
| 2008/0177310 A1 | 7/2008 | Reiley | |
| 2008/0312692 A1 | 12/2008 | Brennan et al. | |
| 2009/0005817 A1 | 1/2009 | Friedrich et al. | |
| 2009/0076549 A1 | 3/2009 | Lim et al. | |
| 2009/0093846 A1 | 4/2009 | Hestad | |
| 2009/0105764 A1 | 4/2009 | Jackson | |
| 2009/0105820 A1 | 4/2009 | Jackson | |
| 2009/0143862 A1* | 6/2009 | Trieu | 623/17.16 |
| 2009/0177196 A1 | 7/2009 | Zlock et al. | |
| 2010/0174317 A1 | 7/2010 | Timm et al. | |
| 2010/0222819 A1 | 9/2010 | Timm et al. | |
| 2010/0331985 A1 | 12/2010 | Gordon et al. | |
| 2011/0196428 A1 | 8/2011 | Panjabi et al. | |
| 2012/0143254 A1 | 6/2012 | Gimbel et al. | |

FOREIGN PATENT DOCUMENTS

| | | |
|---|---|---|
| FR | 2735351 | 12/1996 |
| FR | 2745706 | 9/1997 |
| FR | 2799949 | 4/2001 |
| RU | 2085145 | 7/1997 |
| WO | 9848739 | 11/1998 |
| WO | 0004851 | 2/2000 |
| WO | 0074606 | 12/2000 |
| WO | 101893 | 1/2001 |
| WO | 0156513 | 8/2001 |
| WO | 0245625 | 6/2002 |
| WO | 2004019762 | 3/2004 |
| WO | 2004019828 | 3/2004 |
| WO | 2004019830 | 3/2004 |
| WO | 2004024011 | 3/2004 |
| WO | 2004026188 | 4/2004 |
| WO | 2004041129 | 5/2004 |
| WO | 2004054479 | 7/2004 |
| WO | 2005016194 | 2/2005 |
| WO | 2005067824 | 7/2005 |
| WO | 2005070349 | 8/2005 |
| WO | 2005117725 | 12/2005 |
| WO | 2006066198 | 6/2006 |
| WO | 2006116851 | 11/2006 |

OTHER PUBLICATIONS

Co-pending U.S. Appl. No. 11/655,723 entitled "Artificial Functional Spinal Unit System and Method for Use" to Landry et al. filed Jan. 19, 2007.

Co-pending U.S. Appl. No. 11/655,787 entitled ""Artificial Functional Spinal Unit System and Method for Use"" to Landry et al. filed Jan. 19, 2007.

Co-pending U.S. Appl. No. 11/655,724 entitled ""Artificial Functional Spinal Unit System and Method For Use"" to Landry et al. filed Jan. 19, 2007.

Co-pending U.S. Appl. No. 11/655,790 entitled ""Artificial Functional Spinal Unit System and Method For Use"" to Landry et al. filed Jan. 19, 2007.

Humphreys et al., "Biomechanics of the Kenti (TM) Total Joint Replacement", Presented at the Global Symposium on Motion Preservation Technology, May 9-13, 2006; 3 pages.

Hodges et al., "Biomechanics of the Kenti (TM) Total Joint Replacement", Presented at the Global Symposium on Motion Preservation Technology, May 9-13, 2006; 1 page.

Patel et al., "Changes in Kinematics following Single Level fusion, Single and Bi-Level Charite disc replacement in the Lumbar Spine" Presented at the Global Symposium on Motion Preservation Technology, May 9-13, 2006; 1 page.

U.S. Appl. No. 11/371,170 Entitled "Dynamic Interbody Device" filed Mar. 8, 2006.

PCT Search Report and Written Opinion for International Application No. PCT/US2007/063595 mailed Dec. 11, 2007, 15 pages.

U. S. Patent and Trademark Office "Communication" for U.S. Appl. No. 11/371,182, mailed Jul. 21, 2009.

U. S. Patent and Trademark Office "Communication" for U.S. Appl. No. 11/371,188, mailed Mar. 17, 2009.

U. S. Patent and Trademark Office "Communication" for U.S. Appl. No. 11/371,182, mailed Apr. 24, 2009.

U. S. Patent and Trademark Office "Communication" for U.S. Appl. No. 11/371,328, mailed Mar. 17, 2009.

U. S. Patent and Trademark Office "Communication" for U.S. Appl. No. 11/371,190, mailed Aug. 11, 2008.

U. S. Patent and Trademark Office "Communication" for U.S. Appl. No. 11/655,724, mailed May 27, 2009.

U. S. Patent and Trademark Office "Communication" for U.S. Appl. No. 11/655,787, mailed May 27, 2009.

U. S. Patent and Trademark Office "Communication" for U.S. Appl. No. 11/655,737, mailed May 27, 2009.

U. S. Patent and Trademark Office "Communication" for U.S. Appl. No. 11/655,723, mailed May 27, 2009.

U. S. Patent and Trademark Office "Communication" for U.S. Appl. No. 11/655,790, mailed Jun. 4, 2009.

U. S. Patent and Trademark Office "Communication" for U.S. Appl. No. 11/371,182, mailed Oct. 11, 2007.

U. S. Patent and Trademark Office "Communication" for U.S. Appl. No. 11/371,182, mailed Jun. 9, 2008.

U. S. Patent and Trademark Office "Communication" for U.S. Appl. No. 11/371,182, mailed Dec. 12, 2008.

U. S. Patent and Trademark Office "Communication" for U.S. Appl. No. 11/371,182, mailed Mar. 25, 2009.

Serhan et al. "Biomechanics of the posterior lumbar articulating elements," Neurosurg Focus 2007, 22(1):E1, 6 pages.

Khoueir et al. "Classification of posterior dynamic stabilization devices," Neurosurg Focus, 2007, 22(1):E1, 8 pages.

U. S. Patent and Trademark Office "Communication" for U.S. Appl. No. 11/371,328, mailed Dec. 30, 2009.

U. S. Patent and Trademark Office "Communication" for U.S. Appl. No. 11/134,069, mailed Dec. 30, 2009.

U. S. Patent and Trademark Office "Communication" for U.S. Appl. No. 11/134,055, mailed Jan. 19, 2010.

U. S. Patent and Trademark Office "Communication" for U.S. Appl. No. 11/134,073, mailed Jan. 27, 2010.

U. S. Patent and Trademark Office "Communication" for U.S. Appl. No. 11/134,091, mailed Jan. 26, 2010.

U. S. Patent and Trademark Office "Communication" for U.S. Appl. No. 11/371,182, mailed Feb. 8, 2010.

(56) References Cited

OTHER PUBLICATIONS

U. S. Patent and Trademark Office "Communication" for U.S. Appl. No. 11/134,066, mailed Feb. 18, 2010.
U. S. Patent and Trademark Office "Communication" for U.S. Appl. No. 11/134,079, mailed Feb. 19, 2010.
U. S. Patent and Trademark Office "Communication" for U.S. Appl. No. 11/134,067, mailed Feb. 18, 2010.
U. S. Patent and Trademark Office "Communication" for U.S. Appl. No. 10/777,411, mailed Mar. 5, 2010.
U. S. Patent and Trademark Office "Communication" for U.S. Appl. No. 11/050,632, mailed Mar. 2, 2010.
U. S. Patent and Trademark Office "Communication" for U.S. Appl. No. 11/371,190, mailed Feb. 26, 2010.
U. S. Patent and Trademark Office "Communication" for U.S. Appl. No. 11/134,082, mailed Mar. 12, 2010.
PCT Search Report and Written Opinion for PCT/US2004/025090 mailed on Apr. 11, 2005 (23 pages).
U.S. Patent and Trademark Office "Communication" for U.S. Appl. No. 11/343,933 mailed Nov. 19, 2007.
U.S. Patent and Trademark Office "Communication" for U.S. Appl. No. 11/134,091 mailed Feb. 21, 2008.
U.S. Patent and Trademark Office "Communication" for U.S. Appl. No. 11/134,092 mailed Feb. 21, 2008.
U.S. Patent and Trademark Office "Communication" for U.S. Appl. No. 10/777,411 mailed Mar. 20, 2008.
U.S. Patent and Trademark Office "Communication" for U.S. Appl. No. 11/134,055 mailed Aug. 25, 2008.
U.S. Patent and Trademark Office "Communication" for U.S. Appl. No. 11/343,933 mailed Jun. 30, 2008.
U.S. Patent and Trademark Office "Communication" for U.S. Appl. No. 10/777,411 mailed Mar. 19, 2007.
U.S. Patent and Trademark Office "Communication" for U.S. Appl. No. 10/777,411 mailed Sep. 24, 2007.
U.S. Patent and Trademark Office "Communication" for U.S. Appl. No. 10/777,411 mailed Aug. 29, 2008.
U.S. Patent and Trademark Office "Communication" for U.S. Appl. No. 10/777,411 mailed Dec. 23, 2008.
U.S. Patent and Trademark Office "Communication" for U.S. Appl. No. 11/050,632 mailed Sep. 24, 2008.
U.S. Patent and Trademark Office "Communication" for U.S. Appl. No. 11/050,632 mailed Apr. 16, 2009.
U.S. Patent and Trademark Office "Communication" for U.S. Appl. No. 11/134,066 mailed Dec. 4, 2008.
U.S. Patent and Trademark Office "Communication" for U.S. Appl. No. 11/134,091 mailed Dec. 24, 2008.
U.S. Patent and Trademark Office "Communication" for U.S. Appl. No. 11/134,069 mailed Dec. 24, 2008.
U.S. Patent and Trademark Office "Communication" for U.S. Appl. No. 11/134,069 mailed Jun. 5, 2009.
U.S. Patent and Trademark Office "Communication" for U.S. Appl. No. 11/134,082 mailed Dec. 3, 2008.
U.S. Patent and Trademark Office "Communication" for U.S. Appl. No. 11/345,602 mailed Mar. 31, 2009.
U. S. Patent and Trademark Office "Communication" for U.S. Appl. No. 10/777,411, mailed Jul. 17, 2009.
U. S. Patent and Trademark Office "Communication" for U.S. Appl. No. 11/134,073, mailed Jul. 22, 2009.
U. S. Patent and Trademark Office "Communication" for U.S. Appl. No. 11/134,079, mailed Aug. 14, 2009.
U. S. Patent and Trademark Office "Communication" for U.S. Appl. No. 11/134,082, mailed Aug. 14, 2009.
U. S. Patent and Trademark Office "Communication" for U.S. Appl. No. 11/134,067, mailed Aug. 14, 2009.
U. S. Patent and Trademark Office "Communication" for U.S. Appl. No. 11/050,632, mailed Aug. 25, 2009.
U. S. Patent and Trademark Office "Communication" for U.S. Appl. No. 11/134,066, mailed Sep. 9, 2009.
U. S. Patent and Trademark Office "Communication" for U.S. Appl. No. 11/345,602, mailed Oct. 13, 2009.
U. S. Patent and Trademark Office "Communication" for U.S. Appl. No. 11/371,170, mailed Nov. 4, 2009.
U. S. Patent and Trademark Office "Communication" for U.S. Appl. No. 10/777,411, mailed Oct. 1, 2009.
U. S. Patent and Trademark Office "Communication" for U.S. Appl. No. 11/371,376, mailed Nov. 4, 2009.
International Preliminary Report on Patentability for International Application No. PCT/US2008/051346 mailed Mar. 27, 2009, 23 pages.
International Search Report and Written Opinion for International Application No. PCT/US2008/051346 mailed Sep. 9, 2008, 20 pages.
U. S. Patent and Trademark Office "Communication" for U.S. Appl. No. 11/371,328, mailed Sep. 28, 2009.
U. S. Patent and Trademark Office "Communication" for U.S. Appl. No. 11/371,188, mailed Sep. 25, 2009.
U. S. Patent and Trademark Office "Communication" for U.S. Appl. No. 11/371,190, mailed Apr. 29, 2009.
U. S. Patent and Trademark Office "Communication" for U.S. Appl. No. 11/371,182, mailed Oct. 14, 2009.
U. S. Patent and Trademark Office "Communication" for U.S. Appl. No. 11/371,190, mailed Nov. 7, 2008.
U. S. Patent and Trademark Office "Communication" for U.S. Appl. No. 11/371,190, mailed Oct. 29, 2009.
U. S. Patent and Trademark Office "Communication" for U.S. Appl. No. 11/655,724, mailed Nov. 23, 2009.
U. S. Patent and Trademark Office "Communication" for U.S. Appl. No. 11/655,787, mailed Nov. 23, 2009.
U. S. Patent and Trademark Office "Communication" for U.S. Appl. No. 11/655,737, mailed Nov. 23, 2009.
U. S. Patent and Trademark Office "Communication" for U.S. Appl. No. 11/655,723, mailed Nov. 24, 2009.
U. S. Patent and Trademark Office "Communication" for U.S. Appl. No. 11/371,190, mailed Oct. 11, 2007.
U. S. Patent and Trademark Office "Communication" for U.S. Appl. No. 11/371,181, mailed Oct. 11, 2007.
Co-pending U.S. Appl. No. 11/975,921 entitled "Dampener System for a Posterior Stabilization System With a Variable Length Elongated Member" to Gimbel et al.
Co-pending U.S. Appl. No. 11/975,918 entitled "Dampener System for a Posterior Stabilization System With a Fixed Length Elongated Member" to Gimbel et al.
Co-pending U.S. Appl. No. 11/975,920 entitled "Posterior Stabilization System With Isolated, Dual Dampener Systems" to Gimbel et al.
Co-pending U.S. Appl. No. 11/975,916 entitled "Posterior Stabilization System With Shared, Dual Dampener Systems" to Gimbel et al.
Co-pending U.S. Appl. No. 11/975,917 entitled "Dampener System for a Posterior Stabilization System With a Variable Length Elongated Member" to Gimbel et al.
Co-pending U.S. Appl. No. 11/975,919 entitled "Spinal Stabilization Systems With Dynamic Interbody Devices" to Gimbel et al.
U. S. Patent and Trademark Office "Communication" for U.S. Appl. No. 11/371,190, mailed Apr. 17, 2008.
U. S. Patent and Trademark Office "Communication" for U.S. Appl. No. 11/655,790, mailed Mar. 15, 2010.
U. S. Patent and Trademark Office "Communication" for U.S. Appl. No. 11/134,069, mailed Apr. 19, 2010.
U. S. Patent and Trademark Office "Communication" for U.S. Appl. No. 11/371,188, mailed Apr. 28, 2010.
U. S. Patent and Trademark Office "Communication" for U.S. Appl. No. 11/371,170, mailed May 4, 2010.
U. S. Patent and Trademark Office "Communication" for U.S. Appl. No. 11/526,849, mailed Jun. 1, 2010.
U. S. Patent and Trademark Office "Communication" for U.S. Appl. No. 11/134,082, mailed May 25, 2010.
U. S. Patent and Trademark Office "Communication" for U.S. Appl. No. 10/777,411, mailed Jun. 9, 2010.
U. S. Patent and Trademark Office "Communication" for U.S. Appl. No. 11/371,328, mailed Jun. 17, 2010.
U. S. Patent and Trademark Office "Communication" for U.S. Appl. No. 11/371,188, mailed Jun. 15, 2010.
U. S. Patent and Trademark Office "Communication" for U.S. Appl. No. 11/371,182, mailed Jun. 8, 2010.

(56) References Cited

OTHER PUBLICATIONS

U. S. Patent and Trademark Office "Communication" for U.S. Appl. No. 11/371,190, mailed Aug. 11, 2010.
U. S. Patent and Trademark Office "Communication" for U.S. Appl. No. 11/134,091, mailed Aug. 4, 2010.
U. S. Patent and Trademark Office "Communication" for U.S. Appl. No. 11/975,916, mailed Aug. 4, 2010.
U. S. Patent and Trademark Office "Communication" for U.S. Appl. No. 11/975,917, mailed Aug. 17, 2010.
U. S. Patent and Trademark Office "Communication" for U.S. Appl. No. 11/975,919, mailed Aug. 19, 2010.
U. S. Patent and Trademark Office "Communication" for U.S. Appl. No. 11/371,182, mailed Aug. 25, 2010.
U. S. Patent and Trademark Office "Communication" for U.S. Appl. No. 11/371,188, mailed Sep. 1, 2010.
U. S. Patent and Trademark Office "Communication" for U.S. Appl. No. 10/777,411, mailed Oct. 15, 2010.
U. S. Patent and Trademark Office "Communication" for U.S. Appl. No. 11/371,170, mailed Jul. 12, 2010.
U. S. P.T. O. Notice of Allowance for U.S. Appl. No. 11/134,069, mailed Oct. 13, 2011.
U. S. P.T. O. Final Office Action for U.S. Appl. No. 11/134,055, mailed Nov. 14, 2011.
U. S. P.T. O. Non-Final Office Action for U.S. Appl. No. 12/841,792, mailed Oct. 20, 2011.
U. S. P.T. O. Notice of Allowance for U.S. Appl. No. 11/134,073, mailed Oct. 13, 2011.
U. S. P.T. O. Notice of Allowance for U.S. Appl. No. 11/134,079, mailed Nov. 25, 2011.
U. S. P.T. O. Notice of Allowance for U.S. Appl. No. 11/134,067, mailed Oct. 3, 2011.
U. S. P.T. O. Notice of Allowance for U.S. Appl. No. 11/371,170, mailed Oct. 12, 2011.
U. S. P.T. O. Notice of Allowance for U.S. Appl. No. 11/975,921, mailed Dec. 14, 2011.
U. S. P.T. O. Notice of Allowance for U.S. Appl. No. 11/975,920, mailed Nov. 16, 2011.
E.P. Communication Pursuant to Article 94(3) EPC for Application No. 08713804.6-2310 mailed Nov. 10, 2011.
U. S. Patent and Trademark Office "Communication" for U.S. Appl. No. 11/526,849, mailed Dec. 6, 2010.
U. S. Patent and Trademark Office "Communication" for U.S. Appl. No. 11/371,328, mailed Jan. 6, 2011.
U. S. Patent and Trademark Office "Communication" for U.S. Appl. No. 11/371,170, mailed Jan. 28, 2011.
U. S. Patent and Trademark Office "Communication" for U.S. Appl. No. 11/975,916, mailed Feb. 9, 2011.
U. S. Patent and Trademark Office "Communication" for U.S. Appl. No. 11/975,917, mailed Feb. 4, 2011.
U. S. Patent and Trademark Office "Communication" for U.S. Appl. No. 11/975,919, mailed Feb. 4, 2011.
U. S. P. T. O. Non-Final Office Action for U.S. Appl. No. 11/655,724, mailed Feb. 17, 2012.
U. S. P.T. O. Notice of Allowance for U.S. Appl. No. 11/975,918, mailed Jan. 19, 2012.
U. S. P.T. O. Notice of Allowance for U.S. Appl. No. 11/975,917, mailed Feb. 1, 2012.
U. S. P.T. O. Final Office Action for U.S. Appl. No. 11/975,919, mailed Jan. 27, 2012.
U. S. P.T. O. Final Office Action for U.S. Appl. No. 11/134,091, mailed Feb. 10, 2012.
U. S. P.T. O. Notice of Allowance for U.S. Appl. No. 11/134,082, mailed Jan. 11, 2012.
U. S. P.T. O. Advisory Action for U.S. Appl. No. 11/134,055, mailed Feb. 15, 2012.
J.P. Notice of Reason for Refusal for Japanese Application No. 2008-558536 mailed Jan. 10, 2012. English translation provided by foreign associate.
U. S. Patent and Trademark Office "Communication" for U.S. Appl. No. 11/975,920, mailed Jun. 7, 2011.
U. S. Patent and Trademark Office "Communication" for U.S. Appl. No. 11/975,921, mailed Jun. 9, 2011.
U. S. Patent and Trademark Office "Communication" for U.S. Appl. No. 11/134,055, mailed Jun. 9, 2011.
U. S. Patent and Trademark Office "Communication" for U.S. Appl. No. 11/371,328, mailed Jun. 23, 2011.
U. S. Patent and Trademark Office "Communication" for U.S. Appl. No. 11/975,919, mailed Jul. 21, 2011.
U. S. Patent and Trademark Office "Communication" for U.S. Appl. No. 11/371,170, mailed Aug. 5, 2011.
U. S. Patent and Trademark Office "Communication" for U.S. Appl. No. 11/655,790, mailed Feb. 4, 2011.
U. S. Patent and Trademark Office "Communication" for U.S. Appl. No. 11/975,918, mailed Aug. 15, 2011.
U. S. Patent and Trademark Office "Communication" for U.S. Appl. No. 11/975,916, mailed Sep. 6, 2011.
U. S. Patent and Trademark Office "Communication" for U.S. Appl. No. 11/975,917, mailed Aug. 3, 2011.
U. S. Patent and Trademark Office "Communication" for U.S. Appl. No. 11/134,091, mailed Aug. 12, 2011.
U.S. Patent and Trademark Office "Communication" U.S. Appl. No. 11/526,849, mailed February 23, 2011.
Co-pending U.S. Appl. No. 13/072,511 entitled "Interbody Device Insertion Systems and Methods" to Gimbel et al. filed Mar. 25, 2011.
U. S. Patent and Trademark Office "Communication" for U.S. Appl. No. 11/371,170, mailed May 6, 2011.
U. S. P.T. O. Advisory Action for U.S. Appl. No. 12/841,792, mailed Jul. 19, 2012.
U. S. P.T. O. Final Office Action for U.S. Appl. No. 11/345,602, mailed Aug. 13, 2012.
U. S. P. T. O. Final Office Action for U.S. Appl. No. 11/655,724, mailed Aug. 24, 2012.
U. S. P.T. O. Non-Final Office Action for U.S. Appl. No. 13/306,535, mailed Aug. 24, 2012.
Co-pending U.S. Appl. No. 13/306,535 entitled "Posterior Stabilization Systems With Shared, Dual Dampener Systems" to Gimbel et al., filed Nov. 29, 2011.
Co-pending U.S. Appl. No. 13/072,511 entitled "Intstrumentation for Artificial Functional Spinal Unit System" to Gimbel et al., filed Mar. 25, 2012.
Co-pending U.S. Appl. No. 13/437,604 entitled "Method of Insertng an Expandable Intervertebral Implant Without Overdistraction" to Gordon et al., filed Apr. 2, 2012.
U. S. P.T. O. Notice of Allowance for U.S. Appl. No. 11/134,091, mailed May 4, 2012.
U. S. P.T. O. Final Office Action for U.S. Appl. No. 12/841,792, mailed Mar. 23, 2012.
U. S. P.T. O. Non-Final Office Action for U.S. Appl. No. 11/371,376, mailed Mar. 23, 2012.
U. S. P.T. O. Notice of Allowance for U.S. Appl. No. 11/975,919, mailed May 11, 2012.
U. S. P.T. O. Non-Final Office Action for U.S. Appl. No. 13/306,535, mailed May 24, 2012.
U. S. P.T. O. Non-Final Office Action for U.S. Appl. No. 11/345,602, mailed Mar. 5, 2012.
E.P.O. Report of Deficiencies for European Application No. 07 758 171.8-2310 mailed on Feb. 13, 2012.
J.P. Notice of Reason for Refusal for Japanese Application No. 2009-546510 mailed on Mar. 6, 2012.
U. S. P.T. O. Non-Final Office Action for U.S. Appl. No. 10/634,950, mailed Dec. 1, 2005.
U. S. P.T. O. Final Office Action for U.S. Appl. No. 11/371,376, mailed Oct. 16, 2012.
U. S. P. T. O. Notice of Allowance for U.S. Appl. No. 11/655,724, mailed Oct. 4, 2012.
U. S. P.T. O. Non-Final Office Action for U.S. Appl. No. 11/134,055, mailed Nov. 8, 2012.

(56) References Cited

OTHER PUBLICATIONS

E.P.O. Communication Pursuant to Article 94(3) for European Application No. 07 758 171.8-2310 mailed on Oct. 11, 2012.
U. S. P.T. O. Non-Final Action for U.S. Appl. No. 11/655,737, mailed Mar. 15, 2013.
U. S. P.T. O. Notice of allowance for U.S. Appl. No. 11/975,916 mailed Jan. 28, 2013.
Co pending U.S. Appl. No. 13/784,224 entitled "Interbody Device Insertion Systems and Methods" to Gimbel, filed Mar. 4, 2013.
E.P. Communication Pursuant to Article 94(3) EPC for Application No. 08713804.6-2310 mailed Jan. 22, 2013.

* cited by examiner

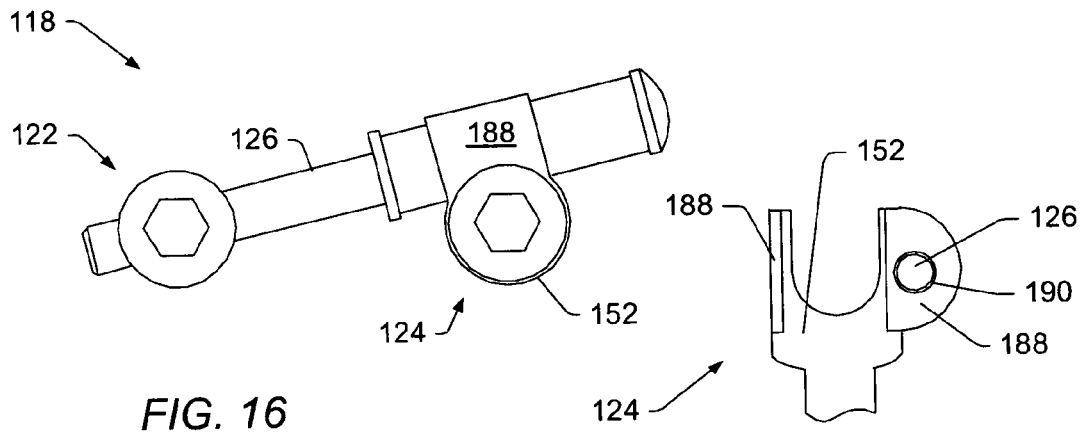
FIG. 16
FIG. 17
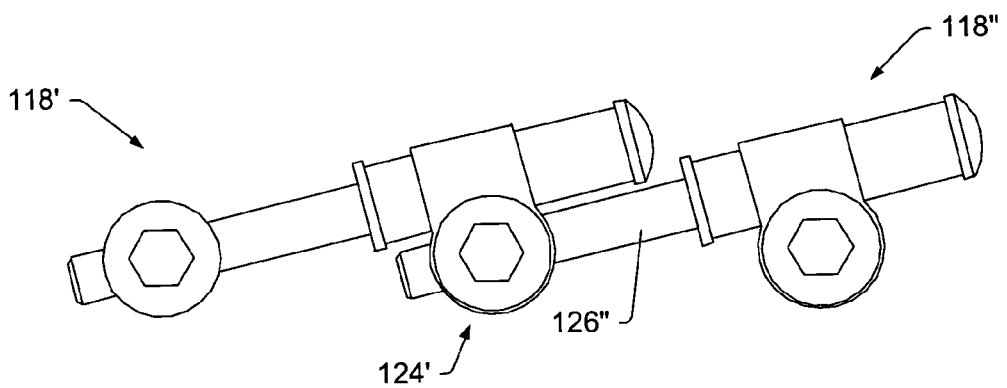
FIG. 18
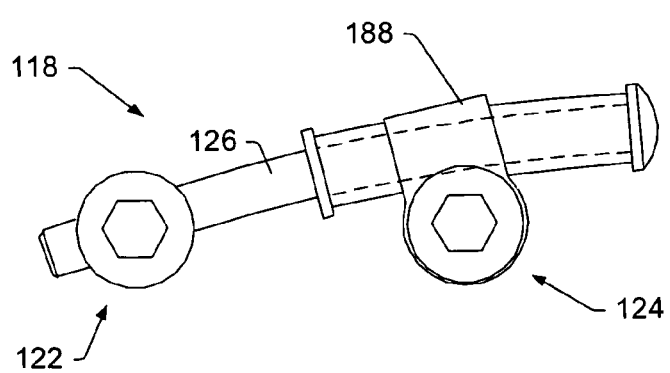
FIG. 19

ARTIFICIAL FUNCTIONAL SPINAL UNIT SYSTEM AND METHOD FOR USE

PRIORITY CLAIM

This application is a continuation-in-part of U.S. patent application Ser. No. 10/634,950 to Gordon et al., filed on Aug. 5, 2003 now U.S. Pat. No. 7,204,853 and entitled "Artificial Functional Spinal Unit Assemblies", which is incorporated herein by reference.

BACKGROUND

1. Field of the Invention

Embodiments of the invention generally relate to functional spinal implant assemblies for insertion into an intervertebral space between adjacent vertebrae of a human spine, and reconstruction of the posterior elements to provide stability, flexibility, and proper biomechanical motion. More specifically, embodiments of the invention relate to artificial functional spinal units including an artificial intervertebral implant that can be inserted via a posterior surgical approach and used in conjunction with one or more dynamic posterior stabilization systems to approach an anatomically correct range of motion and segmental stiffness. Embodiments of the invention may also be inserted via an anterior surgical approach.

2. Description of Related Art

The human spine is a complex mechanical structure including alternating bony vertebrae and fibrocartilaginous discs that are connected by strong ligaments and supported by musculature that extends from the skull to the pelvis and provides axial support to the body. The intervertebral discs provide mechanical cushion between adjacent vertebral segments of the spinal column and generally include two basic components: the nucleus pulposus and the annulus fibrosis. The intervertebral discs are positioned between two vertebral end plates. The annulus fibrosis forms the perimeter of the disc and is a tough outer ring that binds adjacent vertebrae together. The end plates are made of thin cartilage overlying a thin layer of hard cortical bone that attaches to the spongy, cancellous bone of a vertebra. The vertebrae generally include a vertebral foramen bounded by the anterior vertebral body and the neural arch, which consists of two pedicles that are united posteriorly by the laminae. The spinous and transverse processes protrude from the neural arch. The superior and inferior articular facets lie at the root of the transverse process.

The human spine is a highly flexible structure capable of a high degree of curvature and twist in nearly every direction. However, genetic or developmental irregularities, trauma, chronic stress, and degenerative wear can result in spinal pathologies for which surgical intervention may be necessary. In cases of deterioration, disease, or injury, an intervertebral disc, or a portion of the intervertebral disc may be removed from the human spine during a discectomy.

After some discectomies, an intervertebral device may be placed in the disc space to fuse or promote fusion of the adjacent vertebrae. During some procedures, fusion may be combined with posterior fixation to address intervertebral disc and/or facet problems. The fusion procedure (e.g., posterior lumbar interbody fusion) and the posterior fixation procedure may be performed using a posterior approach. The posterior fixation may inhibit motion and promote bone healing. Fusing two vertebrae together may result in some loss of motion. Fusing two vertebrae together may also result in the placement of additional stress on one or more adjacent functional spinal units. The additional stress may cause deterioration of an adjacent functional spinal unit that may result in the need for an additional surgical procedure or procedures.

After some discectomies, an intervertebral dynamic device may be placed in the disc space. The dynamic device may allow for movement of the vertebrae coupled to the disc dynamic device relative to each other. U.S. Pat. No. 4,863,477 to Monson, which is incorporated herein by reference, discloses a resilient dynamic device intended to replace the resilience of a natural human spinal disc. U.S. Pat. No. 5,192,326 to Bao et al., which is incorporated herein by reference, describes a prosthetic nucleus for replacing just the nucleus portion of a human spinal disc. U.S. Patent Application Publication No. 2005/0021144 to Malberg et al., which is incorporated herein by reference, describes an expandable spinal implant. Allowing for movement of the vertebrae coupled to the disc prosthesis may promote the distribution of stress that reduces or eliminates the deterioration of adjacent functional spinal units.

An intervertebral device may be positioned between vertebrae using a posterior approach, an anterior approach, a lateral approach, or other type of approach. A challenge of positioning a device between adjacent vertebrae using a posterior approach is that a device large enough to contact the end plates and slightly expand the space must be inserted through a limited space. This challenge is often further heightened by the presence of posterior osteophytes, which may cause "fish mouthing" of the posterior vertebral end plates and result in very limited access to the disc. A further challenge in degenerative disc spaces is the tendency of the disc space to assume a lenticular shape, which may require a larger implant than can be easily introduced without causing trauma to adjacent nerve roots. The size of rigid devices that may safely be introduced into the disc space is thereby limited. During some spinal fusion procedures using a posterior approach, two implants are inserted between the vertebrae. During some posterior procedures, one or both facet joints between the vertebrae may be removed to provide additional room for the insertion of a fusion device.

The anterior approach poses significant challenges as well. Though the surgeon may gain very wide access to the interbody space from the anterior approach, this approach has its own set of complications. The retroperitoneal approach usually requires the assistance of a surgeon skilled in dealing with the visceral contents and the great vessels, and the spine surgeon has extremely limited access to the nerve roots. Complications of the anterior approach that are approach specific include retrograde ejaculation, ureteral injury, and great vessel injury. Injury to the great vessels may result in massive blood loss, postoperative venous stasis, limb loss, or death. The anterior approach is more difficult in patients with significant obesity and may be virtually impossible in the face of previous retroperitoneal surgery.

Furthermore, disc degeneration is often coupled with facet degeneration. Facet degeneration is addressed using a posterior approach. Thus a second surgical approach may be required if the disc degeneration is treated using an anterior approach. The need to address facet degeneration has led to the development of facet replacement devices. Some facet replacement devices are shown in U.S. Pat. No. 6,419,703 to Fallin et al.; U.S. Pat. No. 6,902,580 to Fallin et al.; U.S. Pat. No. 6,610,091 to Reiley; U.S. Pat. No. 6,811,567 to Reiley; and U.S. Pat. No. 6,974,478 to Reiley et al, each of which is incorporated herein by reference. The facet replacement devices may be used in conjunction with anterior disc replacement devices, but the facet replacement devices are not designed to provide a common center of rotation with the anterior disc replacement devices. The use of an anterior disc replacement device that has a fixed center of rotation contrary to the fixed center of rotation of the facet replacement device may restrict or diminish motion and be counterproductive to the intent of the operation.

Despite the difficulties of the anterior approach, the anterior approach does allow for the wide exposure needed to place a large device. In accessing the spine anteriorly, one of the major structural ligaments, the anterior longitudinal ligament, must be completely divided. A large amount of anterior annulus must also be removed along with the entire nucleus. Once these structures have been resected, the vertebral bodies may need to be over distracted to place the device within the disc space and restore disc space height. Failure to adequately tension the posterior annulus and ligaments increases the risk of device failure and/or migration. Yet in the process of placing these devices, the ligaments are overstretched while the devices are forced into the disc space under tension. Over distraction can damage the ligaments and the nerve roots. The anterior disc replacement devices currently available or in clinical trials may be too large to be placed posteriorly, and may require over distraction during insertion to allow the ligaments to hold them in position.

During some spinal stabilization procedures a posterior fixation system may be coupled to the spine. During some procedures, posterior fixation systems may be coupled to each side of the spine. The posterior fixation systems may include elongated members that are coupled to vertebrae by fasteners (e.g., hooks and screws). In some embodiments, one or more transverse connectors may be connected to the posterior fixation systems to join and stabilize the posterior fixation systems.

During some spinal stabilization procedures, dynamic posterior stabilization systems may be used. U.S. Patent Application Nos. 2005/0182409 to Callahan et al.; 2005/0245930 to Timm et al.; and 2006/0009768 to Ritland, each of which is incorporated herein by reference, disclose dynamic posterior stabilization systems.

SUMMARY

One or more dynamic interbody devices for a spine may be inserted in a disc space between vertebrae. In addition to one or more dynamic interbody devices, at least one dynamic posterior stabilization systems may be coupled to the vertebrae. In an embodiment, a stabilization system for a human spine includes at least one dynamic interbody device configured to be positioned in a disc space between a first vertebra and a second vertebra; a first bone fastener, the first bone fastener configured to couple to the first vertebra; a second bone fastener, the second bone fastener configured to couple to the second vertebra; an elongated member configured to couple to the first bone fastener and the second bone fastener; and a bridge configured to couple to the second bone fastener when the second bone fastener is coupled to the second vertebra. The stabilization system when coupled to the vertebrae may allow for movement of the first vertebra relative to the second vertebra. In some embodiments, one or more bias members may be coupled to the elongated member. At least one of the bias members may provide resistance to movement allowed by at least one dynamic interbody device.

In some embodiments, the bridge inhibits posterior migration of at least one dynamic interbody device. In some embodiments, the position of the bridge may inhibit contact with neural structures when the second bone fastener is coupled to the second vertebra and the bridge is coupled to at least one dynamic device. In some embodiments, the bridge, may be coupled to at least one dynamic interbody device. In some embodiments, the bridge is an integral component of a dynamic interbody device.

In some embodiments, a stabilization system for the human spine includes at least one dynamic interbody device configured to be positioned between a first vertebra and a second vertebra; a first bone fastener having a collar, the first bone fastener configured to couple to the first vertebra; a second bone fastener having a collar, the second bone fastener configured to couple to the second vertebra; an elongated member configured to couple to the collar of the first bone fastener and the collar of the second bone fastener when the first bone fastener and the second bone fastener are coupled to the first vertebra and the second vertebra to allow for movement of the first vertebra relative to the second vertebra; and a bridge configured to couple to the second bone fastener. In some embodiments, the bridge is an integral member of a dynamic interbody device. In some embodiments, the bridge couples to a dynamic interbody device.

In some embodiments, a method of stabilizing a portion of a human spine includes coupling at least one dynamic interbody device to a first vertebra and a second vertebra, wherein at least one dynamic interbody device allows movement of the first vertebra relative to the second vertebra; coupling a first dynamic posterior stabilization system to the first vertebra and the second vertebra, wherein at the first dynamic posterior stabilization device allows movement of the first vertebra relative to the second vertebra to guide movement allowed by at least one dynamic interbody device; coupling a second dynamic posterior stabilization system to the first vertebra and the second vertebra on a contralateral side, wherein at least one dynamic posterior stabilization device allows movement of the first vertebra relative to the second vertebra to guide movement allowed by at least one dynamic interbody device; and coupling a bridge to the first dynamic posterior stabilization system. In some embodiments the method may also include coupling the bridge to at least one dynamic interbody device.

BRIEF DESCRIPTION OF THE DRAWINGS

Advantages of the present invention will become apparent to those skilled in the art with the benefit of the following detailed description and upon reference to the accompanying drawings in which:

FIG. 16 depicts an embodiment of a dynamic posterior stabilization system with a laterally positioned elongated member.

FIG. 17 depicts a front view representation of the second bone fastener depicted in FIG. 16.

FIG. 18 depicts an embodiment of a multi-level dynamic posterior stabilization system.

FIG. 19 depicts an embodiment of a dynamic posterior stabilization system.

Figure 1:
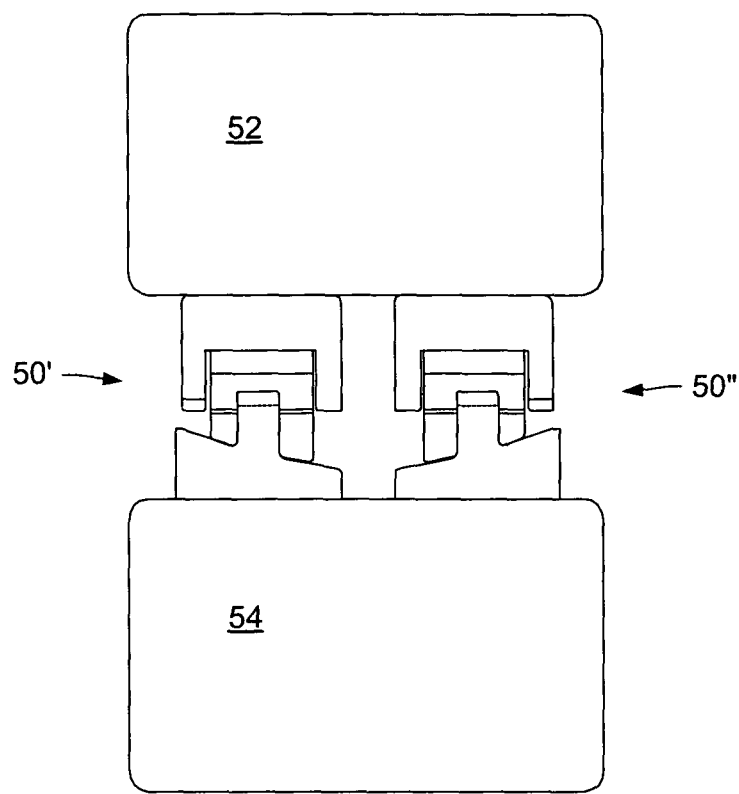
FIG. 1 depicts a schematic view of a portion of an embodiment of a spinal stabilization system.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION

A "functional spinal unit" generally refers to a motion segment of a spine. The functional spinal unit may include two vertebrae, an intervertebral disc between the vertebrae, and the two facet joints between the vertebrae. An "artificial functional spinal unit" refers to a functional spinal unit where one or more of the components of the functional spinal unit are replaced by implants or devices that permit at least some motion of the spine. At least a portion of the intervertebral disc and/or one or both of the facet joints may be replaced by implants or devices during a spinal stabilization procedure.

As used herein, "coupled" includes a direct or indirect joining or touching unless expressly stated otherwise. For example, a first member is coupled to a second member if the first member contacts the second member, or if a third member is positioned between the first member and the second member.

A "dynamic interbody device" generally refers to an artificial intervertebral implant that allows for flexion/extension, lateral bending and/or axial rotation of vertebrae coupled to the device. The dynamic interbody device may replace a portion or all of an intervertebral disc. In some embodiments, a pair of dynamic interbody implants are installed during a spinal stabilization procedure. In some embodiments, a dynamic interbody device is installed using a posterior approach. In other embodiments, a dynamic interbody device may be installed using an anterior approach or other type of approach. In some embodiments, one or more dynamic interbody devices are placed in a disc space between vertebrae, and at least one posterior stabilization system is coupled to the vertebrae. In some embodiments, one or more dynamic interbody devices are placed in the disc space without coupling a posterior stabilization system to the vertebrae.

Dynamic interbody devices may have surfaces that contact vertebrae. In some embodiments, a surface of the dynamic interbody device that contacts a vertebra may include one or more keels, protrusions, and/or osteoconductive/osteoinductive layers or coatings. A keel of the dynamic interbody device may be positioned in a groove formed in a vertebra. The groove may be formed in the vertebra so that the dynamic interbody device will be positioned at a desired location when inserted into the patient. Protrusions of the dynamic interbody device may penetrate an endplate of the vertebra to secure the dynamic interbody device to the vertebra. An osteoconductive/osteoinductive layer may promote bone growth that secures the dynamic interbody device to the vertebra. The osteoconductive/osteoinductive layer may include, but is not limited to a scaffold, a roughened surface, a surface treated with a titanium plasma spray, bone morphogenic proteins, and/or hydroxyapatite. A roughened surface may be formed by chemical etching, by surface abrading, by shot peening, by an electrical discharge process, and/or by embedding particles in the surface.

A dynamic interbody device may include one or more angled surfaces so that the dynamic interbody device provides the patient with a desired amount of lordosis. Dynamic interbody devices that provide different amounts of lordosis may be provided in an instrument kit supplied for a spinal stabilization procedure. For example, the instrument kit for a spinal stabilization procedure may include pairs of dynamic interbody devices that establish 0°, 3°, 6°, 9°, 12° or 15° of lordosis. Pairs of dynamic interbody devices that provide other amounts of lordosis may be provided. The amount of lordosis provided by a dynamic interbody device may be printed or etched on a visible surface of the dynamic interbody device. Other information may also be printed or etched on the visible surface of the dynamic interbody device. Such information may include dimension information (e.g., length, width, and/or height) and whether the dynamic interbody device is to be installed on the left side of the patient or the right side of the patient.

In some embodiments, one or more dynamic interbody devices are installed in a disc space formed in the lumbar region of the spine during a spinal stabilization procedure. The shape and/or size of a dynamic interbody device may depend on a number of factors including surgical approach employed for insertion, intended position in the spine (e.g., cervical or lumbar), and patient anatomy. A dynamic interbody device for the lumbar spine may have a height that is less than about 22 mm. Several sizes of interbody devices may be provided in the instrument kit for the spinal stabilization procedure. In an embodiment, dynamic interbody devices having heights of 6 mm, 8 mm, 10 mm, 12, mm, 14 mm, 16 mm, 18 mm, and 20 mm are provided in the instrument kit for the spinal stabilization procedure. The dynamic interbody devices may include indicia indicating the height of the spinal stabilization devices.

In some embodiments, a single dynamic interbody device may be positioned in a disc space between vertebrae. The dynamic interbody device may be installed using an anterior approach, a posterior approach, or a different type of approach. In some embodiments, the height of the dynamic interbody device may be adjustable during the installation procedure. U.S. Patent Application Publication No. 2005/0278026 to Gordon et al., which is incorporated herein by reference, describes expandable dynamic spinal implants. In some embodiments, insertion instruments may change the separation distance between endplates of the dynamic interbody device. One or more shims may be coupled to the dynamic interbody device to maintain the selected separation distance.

In some embodiments, a pair of dynamic interbody devices may be installed between a pair of vertebrae to establish a stabilization system. In some embodiments, the dynamic interbody device is a bimodal device. Bimodal refers to a device that has two separate curved surfaces to accommodate flexion/extension, lateral bending and/or axial rotation.

FIG. 1 depicts an anterior view of an embodiment of a portion of a stabilization system positioned between vertebrae. Dynamic interbody device 50' may be positioned on a first side of the patient. Dynamic interbody device 50" may be positioned on the contralateral side of the patient. Dynamic interbody device 50' may be the mirror image of dynamic interbody device 50". Dynamic interbody devices 50', 50" may be bimodal devices. Dynamic interbody devices 50', 50" may provide sufficient contact area against end plates of vertebrae 52, 54 to support the spinal column and inhibit subsidence of the vertebrae.

Each dynamic interbody device 50', 50" of the pair of dynamic interbody devices may have a width that is significantly less than the width of a single dynamic interbody device that can be installed in the disc space between first vertebra 52 and second vertebra 54. Using two interbody devices 50', 50" may limit the amount of bone and tissue removal needed for insertion using a posterior approach. Each of the dynamic interbody devices may have a width that is less than 17 mm. In some embodiments, the dynamic interbody devices may be provided in pairs having small, medium or large widths. The instrument kit for the spinal stabilization procedure may include one or more sizes of dynamic interbody devices. In an embodiment, the instrument kit includes dynamic interbody device pairs having medium and large widths.

As used herein a "dynamic posterior stabilization system" generally refers to an apparatus used to replace or supplement a facet joint while allowing for both dynamic resistance and at least some motion of the first vertebra to be stabilized relative to the second vertebra to be stabilized. The first vertebra and the second vertebra may be vertebrae of a functional spinal unit. In some embodiments, bone fasteners of the dynamic posterior stabilization system are secured to the first vertebra and the second vertebra. In some embodiments, a bone fastener of the dynamic posterior stabilization system may be coupled to a vertebra adjacent to the vertebrae of the functional spinal unit being stabilized. The bone fasteners may be coupled to lamina, pedicles, and/or vertebral bodies of the vertebrae. In some embodiments, dynamic posterior stabilization systems may be positioned in three or more vertebrae to form a multi-level stabilization system.

The dynamic posterior stabilization system may replace or supplement a normal, damaged, deteriorated, defective or removed facet joint. The dynamic posterior stabilization system may include bone fasteners, an elongated member, and at least one bias member. The bias member may provide little initial resistance to movement of a first vertebra coupled to the system relative to a second vertebra coupled to the system. Resistance to additional movement of the first vertebra relative to the second vertebra may increase. The increasing resistance provided by the bias member may mimic the behavior of a normal functional spinal unit. The dynamic posterior stabilization system may stabilize the vertebrae, limit the range of motion of the first vertebra relative to the second vertebra, and/or share a portion of the load applied to the vertebrae.

The dynamic posterior stabilization systems disclosed herein may allow for rotational and/or translational motion of an elongated member (e.g., a rod or plate) relative to one or more bone fasteners. The bone fasteners may include threading, barbs, rings or other protrusions that secure the bone fasteners to vertebrae. In some embodiments, the bone fasteners may be cemented or glued to the vertebrae. Bone fasteners may include collars. In some embodiments, a collar of a bone fastener is an integral portion of the bone fastener. In some embodiments, the collar is a separate component that is coupled to at least one other component of the bone fastener. The collar of the bone fastener is the portion of the bone fastener that couples to an elongated member of the dynamic posterior stabilization system. In some embodiments, the bone fasteners are polyaxial pedicle screws and the collars are the upper portions of the polyaxial pedicle screws. In some embodiments, the bone fasteners are bone screws and the collars are plates or other structures that are coupled to the bone screws.

During installation of dynamic interbody devices of a spinal stabilization system, or during installation of a single dynamic interbody device, one or both facet joints of the vertebrae may be removed. A dynamic posterior stabilization system may be installed to replace a removed facet joint. One or both of the dynamic interbody devices of the spinal stabilization system, or the single dynamic interbody device, may be coupled to a dynamic posterior stabilization system. Coupling a dynamic interbody device to the dynamic posterior stabilization system may inhibit backout of the dynamic interbody device from the disc space. Coupling the dynamic interbody device to the dynamic posterior stabilization system may facilitate operation of the dynamic interbody device with the dynamic posterior stabilization system.

In some embodiments, a dynamic posterior stabilization system may be installed without removal of a facet joint. The dynamic posterior stabilization system may be installed after a discectomy, laminectomy, or other procedure. The dynamic posterior stabilization system may change the dynamic resistance that is not normal due to degeneration, disease, loss of a portion of the intervertebral disc and/or tissue damage as a result of the surgery.

A dynamic interbody device and a dynamic posterior stabilization system may include one or more biocompatible metals having a non-porous quality and a smooth finish (e.g., surgical grade stainless steel, titanium and/or titanium alloys). In some embodiments, a dynamic interbody device or dynamic posterior stabilization system may include ceramic and/or one or more other suitable biocompatible materials, such as biocompatible polymers and/or biocompatible metals. Biocompatible polymers may include, but are not limited to, polyetheretherketone resins ("PEEK"), carbon reinforced PEEK, ultra high molecular weight polyethylenes, polyethylenes, polyanhydrides, and alpha polyesters. For example, an implant may be constructed of a combination of biocompatible materials including cobalt chromium alloy, ultra high molecular weight polyethylene, and polycarbonate-urethane or silicone blend.

In some embodiments, dynamic interbody devices and dynamic posterior stabilization systems may be made of non-magnetic, radiolucent materials to allow unrestricted post-operative imaging. Certain material may interfere with x-ray and/or magnetic imaging. Magnetic materials may interfere with magnetic imaging techniques. Most non-magnetic stainless steels and cobalt chrome contain enough iron and/or nickel so that both magnetic imaging and x-ray imaging techniques are adversely affected. Other materials, such as titanium and some titanium alloys, are substantially iron free. Such materials may be used when magnetic imaging techniques are to be used, but such materials are often radio-opaque and sub-optimal for x-ray imagining techniques. Many ceramics and polymers are radiolucent and may be used with both magnetic imaging techniques and x-ray imaging techniques. The dynamic interbody devices and/or the dynamic posterior stabilization systems may include coatings and/or markers that indicate the positions of the devices and/or systems during operative and/or post-operative imaging.

Figure 2:
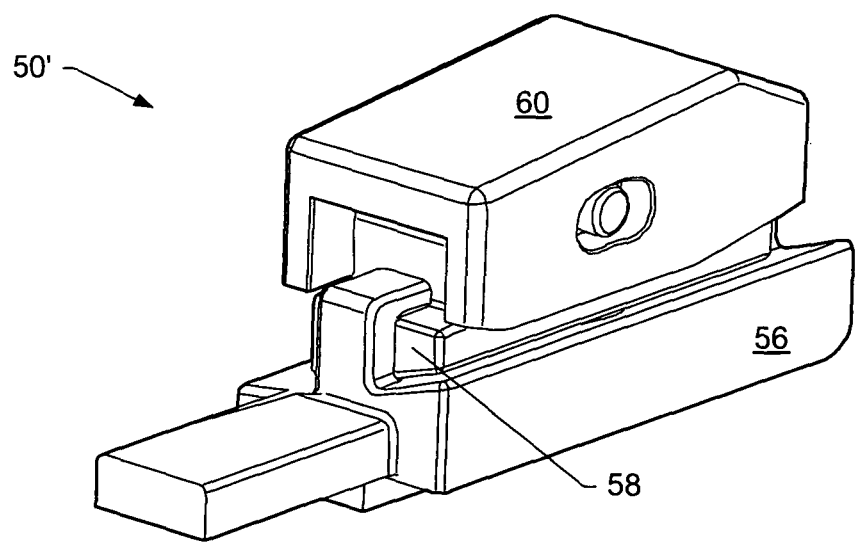
FIG. 2 depicts a perspective view of an embodiment of a dynamic interbody device.

FIG. 2 depicts a portion of an embodiment of dynamic interbody device 50' that may be positioned on a first side of a patient. Dynamic interbody device 50' may include first member 56, second member 58, and third member 60. Dynamic interbody device 50' may be positioned in a disc space between two vertebrae. First member 56, second member 58, and third member 60 may work together to allow for flexion/extension, lateral bending, and/or axial rotation of a vertebra coupled to the first member relative to a vertebra coupled to the third member.

Figures 3, 4:
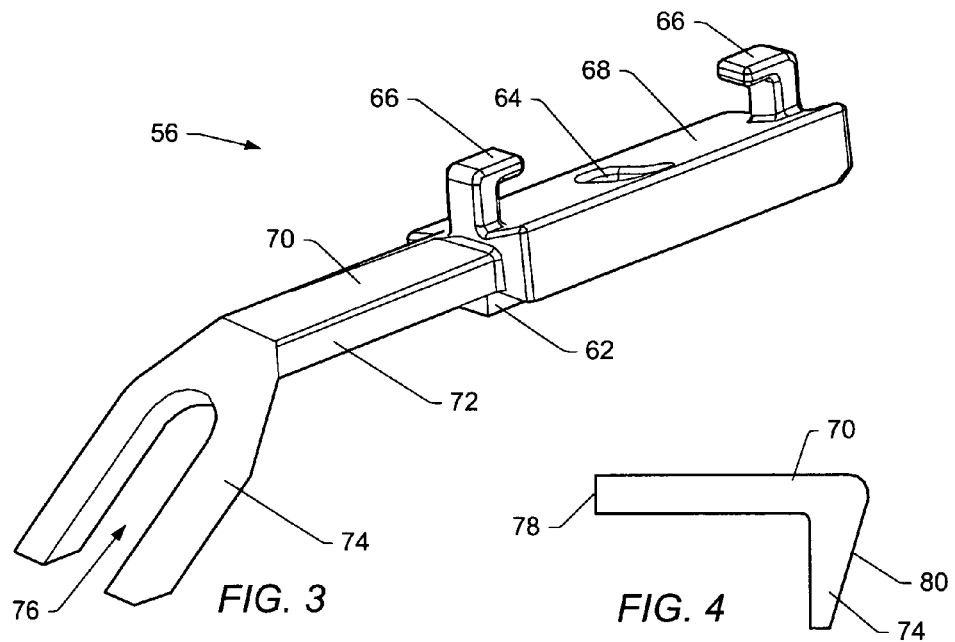
FIG. 3 depicts a perspective view of a first member of the dynamic interbody device depicted in FIG. 2.
FIG. 4 depicts a side view of an embodiment of a separate component bridge.

FIG. 3 depicts an embodiment of first member 56. First member 56 may include keel 62, slot 64, arms 66, arcuate surface 68 and bridge 70. During an implant insertion procedure, keel 62 may be positioned in a channel formed in a vertebra. Keel 62 may couple first member 56 to the vertebra. The bottom surfaces of first member and keel may be osteoconductive/osteoinductive to promote bone growth that secures the first member to the vertebra.

Slot 64 may accommodate a first pin of the second member. In some embodiments, the first member includes a pin that fits in a slot of the second member. The first pin may allow the second member to rotate relative to first member 56 to accommodate axial rotation of the vertebra coupled to the first member relative to the vertebra coupled to the third member of the dynamic interbody device.

Arms 66 may interact with the second member to limit an amount of rotation of the second member relative to first member 56. In some embodiments, the position of arms 66 and/or the size of the second member allows for up to about 4° of axial rotation (e.g. ±2° of rotation from a neutral position). The position of arms 66 and/or the size of the second member may be designed to allow for more or less rotation. In some embodiments, the position of arms 66 and/or the size of the second member allows for about ±1.5° of axial rotation from a neutral position. Arms 66 may also inhibit separation of the second member from first member 56. Gaps may be present between arms 66 and the second member to allow movement of the second member relative to first member 56 that accommodates axial rotation and/or lateral bending of vertebrae coupled to the dynamic interbody device.

A first pin of the second member may slide along a length of slot 64 to accommodate lateral bending of the vertebra coupled to first member 56 relative to the vertebra coupled to the third member of the dynamic interbody device. The curvature of arcuate surface 68 and the length of slot 64 may allow the dynamic interbody device to accommodate about 10° of lateral bending (e.g. ±5° of lateral bending from a neutral position). The length of slot 64 and/or the curvature of arcuate surface 68 may be designed to allow for more or less lateral bending. In some embodiments, the curvature of arcuate surface 68 and the length of slot 64 allows the dynamic interbody device to accommodate about +3° of lateral bending from a neutral position. In some embodiments, arcuate surface 68 may be a spherical portion.

Bridge 70 may couple the dynamic interbody device to a dynamic posterior stabilization system. In some embodiments, bridge 70 is an integral part of first member 56. Bridge 70 may be used to help position keel 62 of first member 56 in the groove formed in the vertebra. In some embodiments, bridge 70 is attached to the dynamic interbody device during the insertion procedure (e.g., by threading, a sliding connection, a snap lock connection or other type of connection). Coupling the bridge to the dynamic interbody device and to the dynamic posterior stabilization system connects the two apparatus together so that one or more centers of rotation that allow for movement of the dynamic interbody device align or substantially align with the curvature of the elongated member of the dynamic posterior stabilization system so that the dynamic posterior stabilization system works in conjunction with the dynamic interbody device to guide motion of the vertebrae coupled to the dynamic interbody device and to the dynamic posterior stabilization system.

In some embodiments, two dynamic interbody devices are placed in the disc space between the vertebrae, and two dynamic posterior stabilization systems are coupled to the vertebrae. Bridges may couple the dynamic interbody devices to the dynamic posterior stabilization systems. The bridges may fix the position of the dynamic interbody devices in working relation to each other so that each of the dynamic interbody devices move during flexion/extension, lateral bending, and/or axial rotation. The bridges may ensure that the dynamic interbody devices work in unison to allow movement of the vertebrae coupled to the dynamic interbody devices.

In some embodiments, a first dynamic interbody device is placed in a prepared disc space between vertebrae. A second dynamic interbody device is also placed in the disc space between the vertebrae. A connector may be coupled to the first dynamic interbody device and the second dynamic interbody device. The connector may link the first dynamic interbody device to the second dynamic interbody device and provide stabilization to the dynamic interbody devices. The connector may inhibit migration of the dynamic interbody devices. The connector may ensure that the dynamic interbody devices work in unison to allow movement of the vertebrae coupled to the dynamic interbody devices. In some embodiments, the connector may slide into the dynamic interbody devices.

Detents, adhesive, setscrews or other fastening systems may inhibits separation of the connector from the dynamic interbody devices.

Bridge 70 may include member 72 and connector 74. In some embodiments, a length of the member is adjustable. A first portion of the member may slide relative to a second portion of the member. A setscrew or other fastening system may set the position of the first portion of the member relative to the second portion of the member when the desired length of the bridge is set. Connector 74 may couple the dynamic interbody device to a posterior stabilization system. Connector 74 may include slot 76. A bone fastener of the posterior stabilization system may be positioned in slot 76 to secure the bridge to a vertebra and to the dynamic posterior stabilization system. In some embodiments, the connector may be a plate or other structure with an opening (e.g., a ring). A shaft of a bone fastener of a dynamic posterior stabilization system may be positioned through the opening to secure the bridge to a vertebra and to the dynamic posterior stabilization system.

In some embodiments, the bridge may be a separate component from the first member. FIG. 4 depicts an embodiment of separate component bridge 70. Connector 74 of bridge 70 may be coupled to the dynamic posterior stabilization system. End 78 of bridge 70 may contact the dynamic interbody device during use to couple the bridge to the dynamic posterior stabilization system and inhibit posterior migration and/or backout of the dynamic is interbody device from the disc space.

The connector of a separate component bridge or the connector of a bridge that is coupled to a dynamic interbody device may include an angled surface. For example, bridge 70 may include angled surface 80. Angled surface 80 may facilitate alignment of the center of a curved elongated member of the dynamic posterior stabilization system with at least one rotation center of the dynamic interbody device (e.g., the rotation centers that control flexion/extension and lateral bending of the dynamic interbody device) so that the dynamic posterior stabilization system works in conjunction with the dynamic interbody device to allow for motion of the vertebra coupled to the dynamic interbody device.

In some embodiments where bridge 70 is a separate component, the dynamic interbody device includes an opening that couples to an inserter. The inserter may couple to the opening of the dynamic interbody device by a detent, threading and/or other reversible coupling system.

The bridge may couple the dynamic interbody device to the dynamic posterior stabilization system. In some embodiments, the bridge may be coupled to the second bone fastener of the dynamic posterior stabilization system. The second bone fastener may be secured to the more caudal of the vertebrae being stabilized. A portion of the bridge may be positioned near the end plate of the more caudal vertebra. The position of the bridge may inhibit contact of the bridge with neural structures (e.g., spinal ganglion) exiting the vertebrae.

Figures 5, 6, 7:
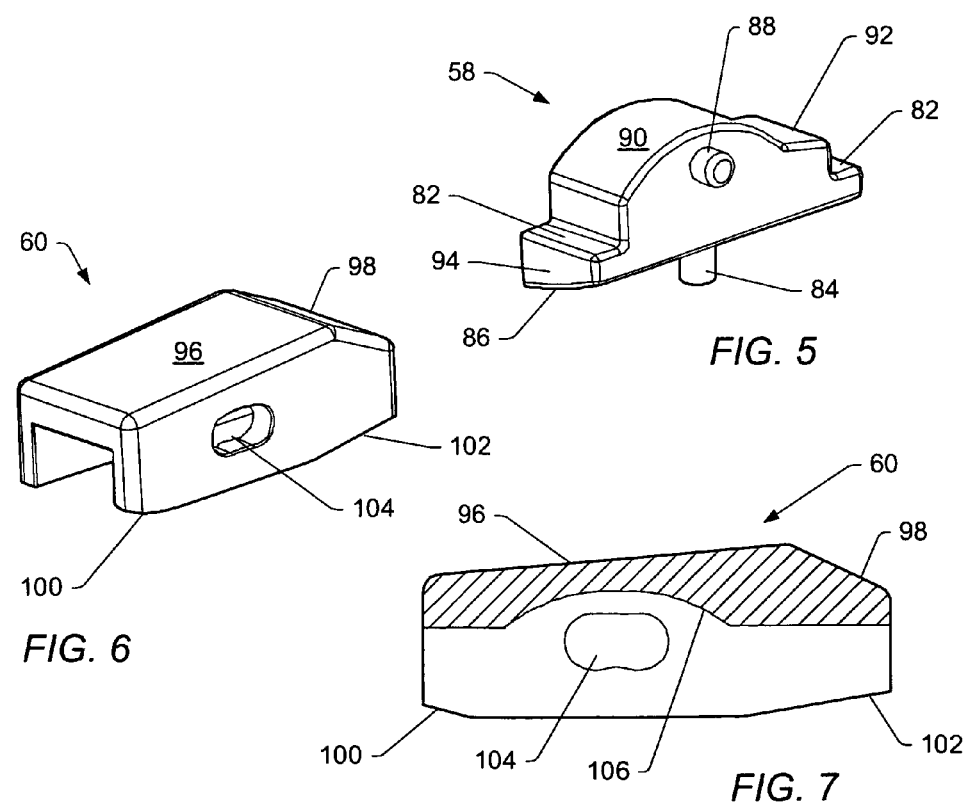
FIG. 5 depicts a perspective view of a second member of the dynamic interbody device depicted in FIG. 2.
FIG. 6 depicts a perspective view of a third member of the dynamic interbody device depicted in FIG. 2.
FIG. 7 depicts a cross-sectional view of a third member of a dynamic interbody device.

FIG. 5 depicts an embodiment of second member 58. Second member 58 may include ledges 82, first pin 84, first arcuate surface 86, second pins 88 (one on each side of the second member), convex surface 90, and upper anterior surface 92. In some embodiments, the second member includes a slot instead of first pin 84. In some embodiments, the second member may includes recesses that accommodate pins of the third member to couple the third member to the second member and allow for flexion/extension of vertebrae coupled to the dynamic interbody device. The recesses may take the place of second pins 88.

Ledges 82 may interact with the arms of the first member to inhibit separation of the first member from second member 58. First pin 84 may be positioned in the slot of the first member to allow for lateral bending and/or axial rotation of the vertebra coupled to the third member relative to the vertebra coupled to the first member. First arcuate surface 86 may have a curvature that complements the curvature of the arcuate surface of the first member.

Second pin 88 may couple second member 58 to the third member. Curved surface 90 may interact with a curved surface of the third member to allow for flexion/extension of the vertebra coupled to the third member relative to the vertebra coupled to the first member. In some embodiments, curved surface 90 is convex and the curved surface of the third member is concave. In some embodiments, the curved surface of the second member is concave and the curved surface of the third member is convex.

The radius of curved surface 90 and the radius of the curved surface of the third member may be small so that translational movement of the vertebra coupled to the third member relative to the vertebra coupled to the first member is kept within a proper range during flexion or extension of the vertebrae. In some embodiments, the radial center of curved surface 90, and the corresponding radial center of the curved surface of the third member, may be located towards posterior end 94 of second member 58 to limit the amount of posterior translation during extension.

In some embodiments, upper anterior surface 92 is a contact surface. A lower anterior surface of the third member may contact upper anterior surface 92 when the dynamic interbody device is at maximum flexion.

FIG. 6 depicts an embodiment of third member 60. FIG. 7 depicts a cross-sectional view of an embodiment of third member 60. Third member 60 may include outer surface 96, lead surface 98, angled lower posterior surface 100, angled lower anterior surface 102, slots 104, and curved surface 106. One slot 104 may be formed on each side of third member 60. At least a portion of outer surface 96 may be sloped to provide a desired amount of lordosis between the vertebrae coupled to the first member and third member 60. Curved surface 106 may be complementary to the curved surface of the second member to allow for flexion and/or extension of the vertebra coupled to the first member relative to the vertebra coupled to the third member.

During insertion of the dynamic interbody device in a disc space, the vertebrae may be distracted so that the disc space has a height that is less than the height of the dynamic interbody device. Lead surface 98 may contact one of the vertebrae and provide force against the vertebra that distracts the vertebrae to allow for insertion of the dynamic interbody device.

In some embodiments, angled lower posterior surface 100 and angled lower anterior surface 102 are contact surfaces. In some embodiments, only one side of the third member includes an angled lower posterior surface and an angled lower anterior surface. In some embodiments, both sides of the third member include angled lower posterior surfaces and angled lower anterior surfaces. Having two angled lower posterior surfaces and two angled lower anterior surfaces may allow the third member to be used in a right dynamic interbody device or a left dynamic interbody device, thus eliminating the need for different left and right third members.

Angled posterior surface 100 may contact the arcuate surface of the first member when the dynamic interbody device is at maximum extension. The dynamic interbody device may allow for a maximum of about 15° of extension from the neutral position. Angled posterior surface 100, the geometry of one or both slots 104, and/or the geometry of the second member may be designed so that the dynamic interbody device has a smaller or a larger maximum angle of extension from the neutral position. In some embodiments, the dynamic interbody device allows for a maximum of about 7° of extension from the neutral position.

Angled lower anterior surface 102 may contact the arcuate surface of the first member when the dynamic interbody device is at maximum flexion. The dynamic interbody device may allow for a maximum of about 20° of flexion from the neutral position. Angled lower anterior surface 102, the geometry of one or both slots 104, and/or the geometry of the second member may be designed so that the dynamic interbody device has a smaller or a larger maximum angle of flexion from the neutral position. In some embodiments, the dynamic interbody device allows for a maximum of about 7° of flexion from the neutral position. In some embodiments, the maximum amount of flexion allowed by the dynamic interbody device is different from the maximum amount of extension. For example, an embodiment of a dynamic interbody device allows for a maximum of about 15° of flexion and a maximum of about 10° of extension.

The second pins of the second member may be positioned in slots 104 to couple third member 60 to the second member. Slots 104 may accommodate rotational movement and translational movement of third member 60 relative to the second member during flexion and extension.

Figure 8:
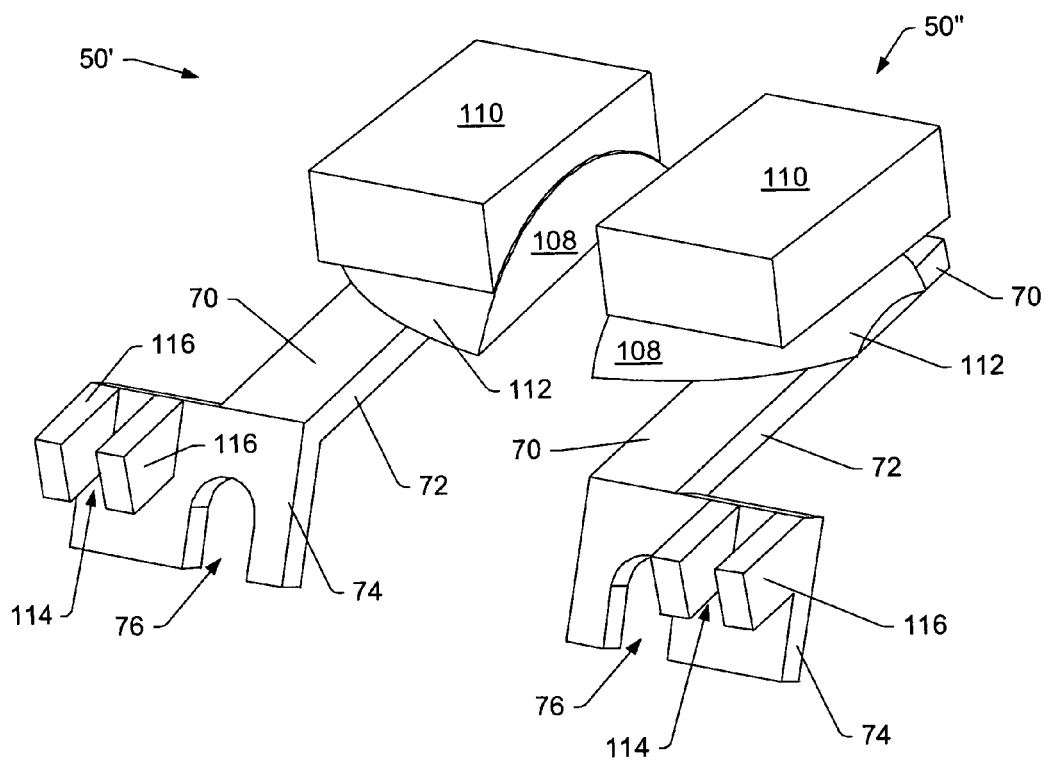
FIG. 8 depicts a perspective view of embodiments of dynamic interbody devices.

FIG. 8 depicts an embodiment of dynamic interbody devices 50', 50". Each dynamic interbody device 50', 50" may include bridge 70, convex member 108 and concave member 110. Convex member 108 and concave member 110 may be coupled to vertebrae. One or more removable members of a dynamic interbody device may initially hold the position of convex member 108 constant relative to concave member 110. After the dynamic interbody device is positioned in a disc space between vertebrae, the removable member or removable members may be removed to allow concave member 110 the ability to move relative to convex member 108.

Curved surface 112 of convex member 108 may have the contour of an outer surface of a portion of a sphere. Concave member 110 may have a curved surface that is complementary to curved surface 112 of convex member 108 to allow for flexion/extension, lateral bending, and axial rotation of the vertebra coupled to convex member 108 relative to the vertebra coupled to concave member 110. In an embodiment, convex member 108 includes a protrusion that extends into a recess of the concave member 110. In an embodiment, convex member 108 includes a recess and concave member 110 includes a protrusion that extends into the recess. The size of the recess may be designed to limit the available range for flexion, extension, lateral bending and/or axial rotation.

Bridge 70 may include elongated portion 72 and connector 74. A section of elongated portion 72 may be a keel for the dynamic interbody device that is positionable in a channel formed in a vertebra. The channels formed in the vertebra for the two dynamic interbody devices may be formed to the same depth and the same distance away from a center line of the vertebra so that the spherical portions of the right dynamic interbody device is in working relation to the spherical portion of the left dynamic interbody device.

In some embodiments, a section of elongated portion 72 may be bendable. Bending elongated portion 72 may allow the dynamic interbody device to be conformed to the patient so that connector 74 can be coupled to a dynamic posterior stabilization system.

Connector 74 may include slot 76 and channel 114 between arms 116. A portion of a bone fastener may be positioned in slot 76 to couple the dynamic interbody device to a bone fastener. Coupling the bone fastener to the dynamic interbody device may inhibit backout of the dynamic interbody device from the disc space between the vertebrae. Coupling the bone fastener to the dynamic interbody device may allow for alignment of the center of rotation of the dynamic interbody device with the center of rotation of a curved elongated member of the dynamic posterior stabilization system so that the dynamic interbody device works in conjunction with the dynamic posterior stabilization system to allow for movement of the vertebrae coupled to the dynamic interbody device.

An elongated member of a posterior stabilization system or dynamic posterior stabilization system may be positioned in channel 114 between arms 116. The elongated member may be coupled to connector 74 to inhibit removal of the elongated member from channel 114. The elongated member of a dynamic posterior stabilization system may be coupled to connector 74 such that translational and/or rotational movement of the elongated member relative to arms 116 is not inhibited.

Figure 9:
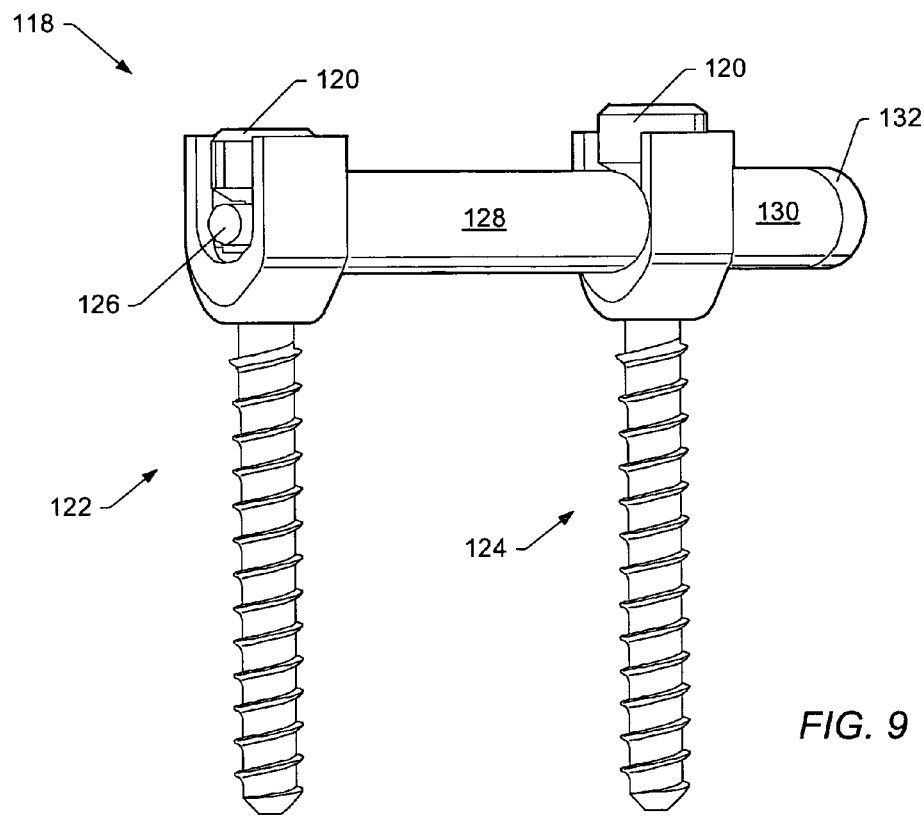
FIG. 9 depicts a perspective view of an embodiment of a posterior stabilization system.

FIG. 9 depicts an embodiment of dynamic posterior stabilization system 118. Dynamic posterior stabilization system 118 may include closure members 120; first bone fastener 122; second bone fastener 124; elongated member 126; and bias members 128, 130. In some embodiments, first bone fastener 122 is positioned in the more upper of the vertebrae to be stabilized. In other embodiments, first bone fastener is positioned in the lower of the vertebrae to be stabilized.

When closure member 120 couples elongated member 126 to first bone fastener 122, movement of the elongated member relative to the first bone fastener may be inhibited. When closure member 120 couples elongated member 126 to second bone fastener 124, translational and/or rotational movement of the elongated member relative to the second bone fastener may be possible. The ability to have translational movement of elongated member 126 relative to second bone fastener 124 may allow dynamic posterior stabilization system 118 to accommodate flexion, extension and lateral bending of a first vertebra coupled to the dynamic posterior stabilization system relative to a second vertebra coupled to the dynamic posterior stabilization system. The ability to have rotational movement of elongated member 126 relative to second bone fastener 124 may allow dynamic posterior stabilization system 118 to accommodate axial rotation of the first vertebra coupled to the dynamic posterior stabilization system relative to the second vertebra coupled to the dynamic posterior stabilization system.

Figure 10:
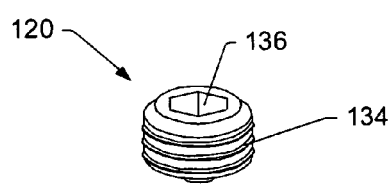
FIG. 10 depicts a perspective view of an embodiment of a closure member.

FIG. 10 depicts an embodiment of closure member 120. Closure member 120 may couple the elongated member of the dynamic posterior stabilization system to the first bone fastener or to the second bone fastener. Closure member 120 may include threading 134 or other structure that secures the closure member to a collar of the first bone fastener 122 or to a collar of the second bone fastener. Closure member 120 may include tool opening 136. A portion of a driver may be inserted into tool opening 136 to facilitate attaching closure member 120 to the collar of the first bone fastener or to the collar of the second bone fastener.

Closure members may be other types of fasteners, including but not limited to clips and snap on connectors. In some embodiments, the closure member coupled to the first bone fastener may be different from the closure member coupled to the second bone fastener. For example, the closure member used to secure the elongated member to the first bone screw may be a closure member as depicted in FIG. 10, while a closure member used to couple the elongated member to the second bone fastener may be a clip that allows the elongated member to move relative to the second bone fastener.

As shown in FIG. 9, dynamic posterior stabilization system 118 includes elongated member 126. Elongated member 126 may be a rod, bar, plate, combination thereof, or other type of member coupled to first bone fastener 122 and second bone fastener 124. In some embodiments where the dynamic posterior stabilization system is to be used with a dynamic interbody device, elongated member 126 may be bent so that the elongated member has a curvature that facilitates the use of the dynamic posterior stabilization system in conjunction with the dynamic interbody device. In embodiments where the dynamic posterior stabilization system is not used in conjunction with a dynamic interbody device, the elongated member may be straight or curved. Elongated members with appropriate curvature may be included in the instrument kit for the spinal stabilization procedure.

Figure 11:
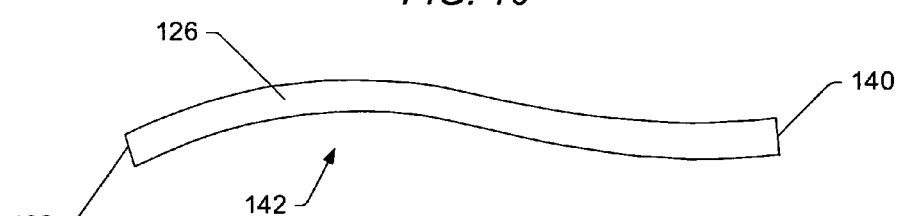
FIG. 11 depicts a side view of an embodiment of an elongated member.

FIG. 11 depicts an embodiment of bent elongated member 126. In an embodiment, a portion of elongated member 126 near first end 138 is secured to the first bone fastener of the dynamic posterior stabilization system so that movement of the elongated member relative to the first bone fastener is inhibited. A portion of elongated member 126 near second end 140 may be coupled to the second bone fastener of the dynamic posterior stabilization system so that translational movement and or rotational movement of the elongated member relative to the second bone fastener is allowed. In some embodiments, concave portion 142 of elongated member 126 may be oriented to face the vertebrae coupled to the dynamic posterior stabilization system so that a center of the curve aligns or substantially aligns with the center or centers of rotation of the dynamic interbody device that allow for flexion/extension and/or lateral bending. The alignment or substantial alignment allows the dynamic posterior stabilization system and the dynamic interbody device to simultaneously accommodate flexion/extension and/or lateral bending of the vertebrae being stabilized. In some embodiments, a portion of elongated member 126 near second end 140 may be bent so that the elongated member does not contact or approach a vertebra during patient movement.

As shown in FIG. 9, an end of elongated member 126 near second bone fastener 124 may include stop 132. Stop 132 may retain bias member 130 on elongated member 126. In some embodiments, the position of the stop may be adjustable along the length of the elongated member. A fixed position stop or an adjustable position stop may be used in conjunction with bias member 128 instead of using the collar of first bone fastener 122 as the stop for bias member 128. In some embodiments, a removable stop may initially maintain bias member 128 in compression. In some embodiments, a removable stop may initially maintain bias member 128 in compression. The removable stops may facilitate coupling elongated member 126 to second bone fastener 124. After elongated member 126 is coupled to second bone fastener 124, the removable stops may be removed so that the bias members can accommodate movement of the elongated member relative to the second bone fastener caused by flexion/extension and/or lateral bending. In some embodiments, an insertion instrument may hold bias members 128, 130 in compression when elongated member 126 is being coupled to first bone fastener 122 and second bone fastener 124.

Bias members 128, 130 may surround or partially surround elongated member 126. Bias members 128, 130 may be stacks of elastic washers, elastic tubes, springs, or other systems that provide resistance to compression. In some embodiments, bias members 128, 130 may be formed of biocompatible polymeric material. For example, bias members 128, 130 may be formed of silicone-urethane co-polymer.

Bias members 128, 130 may transmit little or no force to second bone fastener 124 when dynamic posterior stabilization system 118 is in a neutral position. If second bone fastener 124 is coupled to the more caudal vertebra of the vertebrae to be stabilized, compression of bias member 128 may accommodate translational movement of elongated member 126 caused by extension and/or lateral bending of the vertebrae coupled to dynamic posterior stabilization system 118. If second bone fastener 124 is coupled to the more caudal vertebra of the vertebrae to be stabilized, compression of bias member 130 may accommodate translational movement of elongated member 126 caused by flexion and/or lateral bending of the vertebrae coupled to dynamic posterior stabilization system 118.

Bias member 128 may accommodate up to about 3 mm of travel of second bone fastener 124 towards first bone fastener 122. Bias member 130 may accommodate up to about 2 mm of travel of second bone fastener 124 away from first bone fastener 122.

In some embodiments, bias member 128 and bias member 130 are the same. For example, bias members 128, 130 may be stacks of washers. In some embodiments, bias member 128 is different than bias member 130. For example, bias member 128 is a spring, and bias member 130 is an elastic tube.

Figure 12:
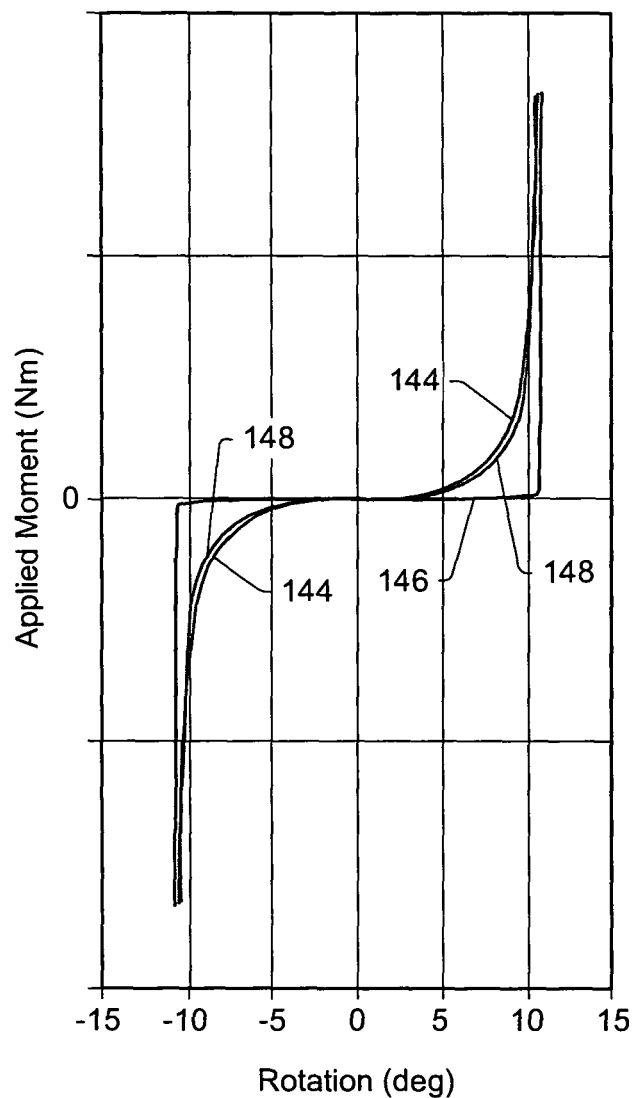
FIG. 12 depicts a plot of applied moment versus rotation.

Bias members 128, 130 may allow dynamic posterior stabilization system 118 to provide stability while still allowing for anatomical motion and dynamic resistance that mimics normal segmental stiffness of the spine. Knowledge of the elastic properties (e.g., the amount of compression per degree of rotation) of the material chosen for bias members 128, 130 allows the length of the bias members placed on the elongated member to be selected so that the dynamic posterior stabilization system provides a desired amount of resistance. FIG. 12 depicts a plot of the applied moment versus the amount of rotation for an intact (normal) functional spinal unit (plot 144), for an unconstrained functional spinal unit (plot 146), and for a functional spinal unit with a dynamic posterior stabilization system (plot 148). The slope of the curves at each point represents spinal stiffness. The neutral zone is the low stiffness region of the range of motion. The dynamic posterior stabilization system may allow for stabilization of the spine while providing substantially unconstrained motion within the neutral zone and increasing resistance to rotation within the elastic zone. The stiffness of vertebrae supported by the dynamic posterior stabilization system may closely mimic the stiffness of a normal functional spinal unit. The behavior of the dynamic posterior stabilization system may closely mimic the normal kinematics of the functional spinal unit.

Figures 13, 14, 15:
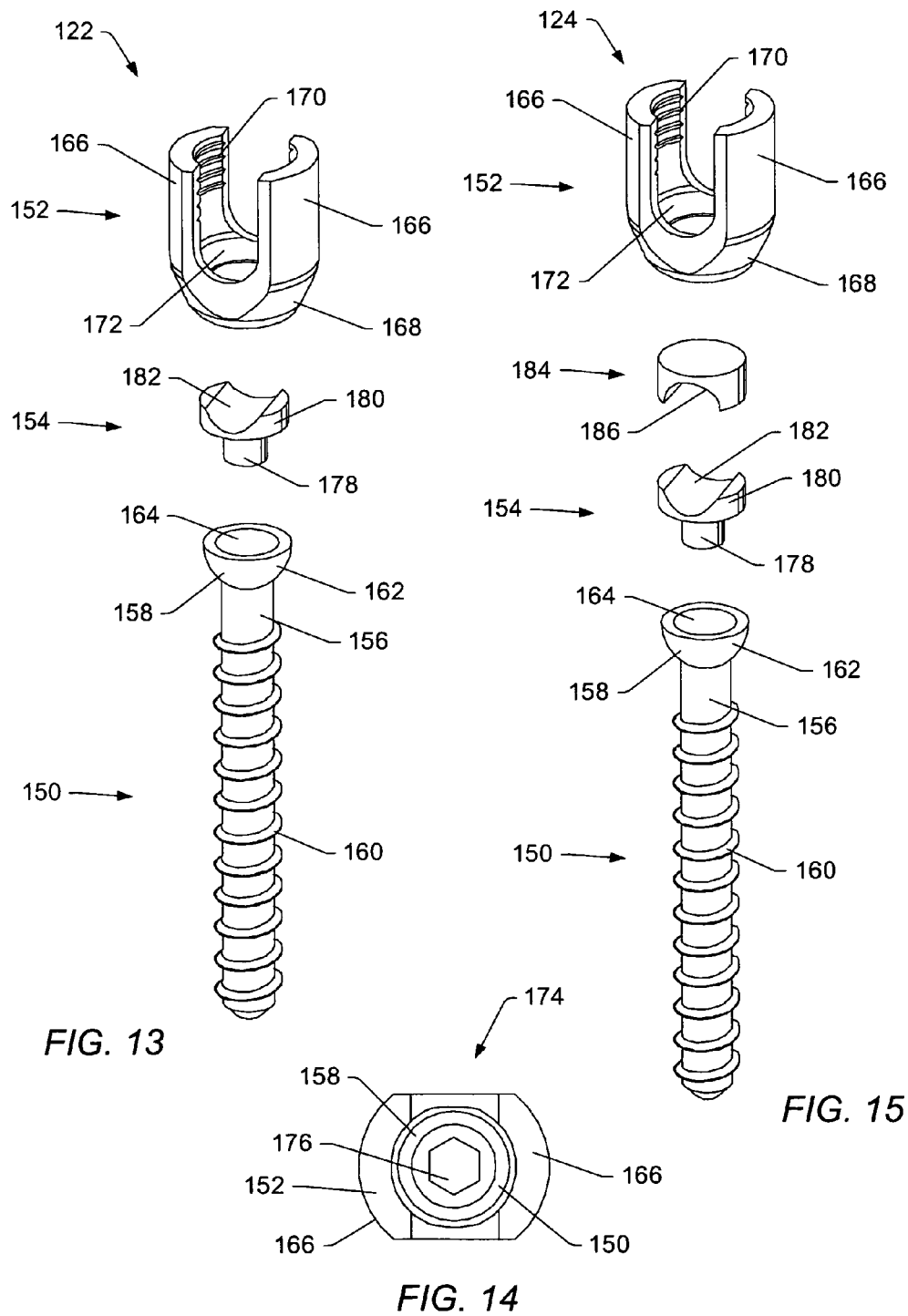
FIG. 13 depicts the components of an embodiment of a first bone fastener of a dynamic posterior stabilization system.
FIG. 14 depicts a top view of an embodiment of a fastener and collar combination for a bone fastener.
FIG. 15 depicts the components of an embodiment of a second bone fastener of a dynamic posterior stabilization system.

FIG. 13 depicts the components of an embodiment of first bone fastener 122. First bone fastener 122 may include fastener 150, collar 152, and saddle 154. Fastener 150 may include shaft 156 and head 158. Shaft 156 may secure first bone fastener 122 to bone (e.g. a vertebra). Shaft 156 may include threading 160 that secures the shaft to the bone.

A portion of outer surface 162 of head 158 may have a spherical contour complementary to a portion of spherically contoured inner surface 172 of collar 152. The shape of outer surface 162 and inner surface 172 of collar 152 may allow for polyaxial positioning of the collar relative to fastener 150. Inner surface 164 of head 158 may be spherically contoured. The spherical contour of inner surface 164 may allow saddle 154 to be positioned in fastener 150 at a desired angle to accommodate the position of collar 152 relative to the fastener.

Collar 152 may include arms 166 and lower body 168. A portion of the elongated member may be positioned in the slot between arms 166. A portion of the inner surfaces of arms 166 may include threading 170 that is complementary to threading of the closure member used to secure the elongated member to first bone fastener 122. Portion 172 of the inner surface of lower body 168 may have a spherically contoured section that complements the spherical contour of outer surface 162 of fastener head 158 to allow for polyaxial positioning of collar 152 relative to fastener 150.

Head 158 of fastener 150 may be positioned in collar 152 to form a fastener and collar combination. FIG. 14 depicts a top view of fastener and collar combination 174. When head 158 is positioned in collar 152, separation of the fastener from the collar may be difficult. Several fastener and collar combinations 174 may be provided in an instrument kit for a dynamic spinal stabilization procedure. The instrument kit may include several combinations 174 with fasteners 150 of varying lengths. For example, the kit may include fastener and collar combinations with fastener having lengths from about 30 mm to about 75 mm in 5 mm increments. In some embodiments, collar 152 of each combination 174 is stamped, printed or etched with the length of fastener 150. Fasteners 150 and/or collars 152 of combinations 174 in the instrument kit may be color coded to indicate the length of the fasteners. For example, the collars of all combinations in the instrument kit with fasteners 150 that are about 30 mm in length have an orange color, the collars of all combinations in the instrument kit with fasteners that are about 35 mm in length have a yellow color, and the collars of all combinations with fasteners that are about 40 mm in length have a green color. Additional colors may be used for additional sizes.

Fastener 150 may include tool opening 176. Tool opening 176 may complement a head of a driver. The driver may be used to insert fastener 150 into bone. The driver may be included in the instrument kit for the spinal stabilization procedure. In some embodiments, arms 166 may include flats, recesses or openings that engage insertion tools or guides.

Referring to FIG. 13, saddle 154 may have post 178 and support 180. Saddle 154 may be positioned in fastener 150 after the fastener and collar combination has been inserted into a vertebra. Post 178 may be positioned in fastener 150. Post 178 may be angled within head 158 of fastener 150 so that saddle 154 can accommodate polyaxial positioning of collar 152 relative to the fastener. In some embodiments, a retaining ring inhibits separation of saddle 154 from fastener 150.

Support 180 may include groove 182. A portion of the elongated member of the dynamic posterior stabilization system may be positioned in groove 182. In some embodiments, saddle 154 and/or collar 152 are shaped so that groove 182 aligns with the slot formed between arms 166 of collar 152 when the saddle is placed in the collar.

A portion of the elongated member may be positioned in groove 182. The closure member for first bone fastener 122 may be threaded on collar 152 and tightened against elongated member 126. In some embodiments, the closure member may include one or more points or edges that bite into the elongated member when the closure member is tightened against the elongated member. When the closure member is tightened against the elongated member, the position of collar 152 relative to fastener 150 may become fixed, and movement of the elongated member relative to first bone fastener may be inhibited.

FIG. 15 depicts an embodiment of second bone fastener 124. Second bone fastener 124 may include fastener 150, collar 152, saddle 154, and cover 184. Fastener 150, collar 152, and saddle 154 of second bone fastener 124 may be substantially the same as the fastener, collar and saddle of the first bone fastener. Cover 184 may include groove 186.

Saddle 154 may be positioned in collar 152 after the fastener and collar combination are inserted in a vertebra. A portion of the elongated member may be positioned in groove 182 of saddle 154. Cover 184 may be positioned on top of the elongated member. The radius of groove 186 may be larger than the radius of the portion of the elongated member positioned in the groove. The closure member for second bone fastener 124 may be threaded on collar 152 and tightened against cover 184. In some embodiments, the closure member may include one or more points or, edges that bite into cover 184 when the closure member is tightened against the cover. The position of collar 152 relative to fastener 150 may become fixed when the closure member is tightened against cover 184. Having the radius of groove 186 larger than the radius of the portion of the elongated member positioned in the groove may allow translational movement and/or rotational movement of the elongated member relative to second bone fastener 124 when the closure member couples the elongated member to the second bone fastener.

When a closure member secures the elongated member between saddle 154 and cover 184, significant change in height of the elongated member relative to second bone fastener 124 may be inhibited. Inhibiting height change of the elongated member relative to second bone fastener may allow the dynamic posterior stabilization system to share a portion of the shear load applied to a dynamic interbody device or intervertebral disc between the vertebrae being stabilized.

In some dynamic posterior stabilization system embodiments, the elongated member may be positioned lateral to the first bone fastener and/or the second bone fastener. FIG. 16 depicts a top view representation of an embodiment of dynamic posterior stabilization system 118 where elongated member 126 is positioned lateral to second bone fastener 124. A closure member may secure elongated member 126 to first bone fastener 122 so that movement of the elongated member relative to the first bone fastener is inhibited.

Second bone fastener 124 may include member 188. A portion of member may slide over or into a portion of collar 152 of second bone fastener 124. The connection between the collar and member may inhibit rotation of member 188 relative to collar 152. A closure member may secure member 188 to collar 152 and second bone fastener 124. When the closure member secures member 188 to collar 152 movement of second bone fastener 124 relative to elongated member 126 is allowed. Second bone fastener 124 may be able to move axially relative to elongated member 126 to accommodate flexion/extension and/or lateral bending of vertebrae coupled to the dynamic posterior stabilization system. Second bone fastener 124 may also be able to rotate relative to elongated member 126 to accommodate axial rotation of vertebrae coupled to the dynamic posterior stabilization system.

FIG. 17 depicts a front view of a portion of second bone fastener 124 of FIG. 16 with member 188 coupled to collar 152 of the second bone fastener. Member 188 may include slot 190. A portion of elongated member 126 may pass through slot 190. Slot 190 and/or the portion of elongated member 126 that can pass through slot may have cross sectional shapes that accommodate rotation of second bone fastener 124 relative to the elongated member so that the dynamic posterior stabilization system is able to accommodate axial rotation of vertebrae being stabilized. Second bone fastener 124 may also be able to move axially along elongated member 126 so that the dynamic posterior stabilization system can accommodate flexion/extension and/or lateral bending of vertebrae being stabilized.

Placement of the elongated member adjacent to the second bone fastener may allow for construction of a multi-level dynamic posterior stabilization system. FIG. 18 depicts a multi-level dynamic posterior stabilization system that includes dynamic posterior stabilization system 118' and dynamic posterior stabilization system 118". Elongated member 126" of dynamic posterior stabilization system 118" may be positioned in and secured to the collar of second bone fastener 124' of dynamic posterior stabilization system 118'. A mirror image dynamic posterior stabilization system construction may be installed on the contralateral side of the spine.

During lateral bending of a first vertebra relative to a second vertebra, the geometry of the facet joints may cause some axial rotation to occur. In some embodiments, the dynamic posterior stabilization system may be designed to cause some axial rotation during lateral bending. FIG. 19 depicts a top view representation of dynamic posterior stabilization system 118 that may introduce some axial rotation when lateral bending occurs. All of elongated member 126 or a portion of the elongated member that passes through member 188 may have a non-circular cross section. The passage of the opening for the elongated member through member 188 may be at an angle. In some embodiments, the orientation of the slot for elongated member 126 at the entrance into member 188 may be different than the orientation of the slot for the elongated member at the exit of the member. Interaction of elongated member 126 with member 188 may allow for some automatic rotation of second bone fastener 124 relative to the elongated member when the second bone fastener moves laterally relative to first bone fastener 122.

In some dynamic posterior stabilization system embodiments, the elongated member may be at a substantially fixed height relative to the second bone fastener. In some dynamic posterior stabilization system embodiments, the elongated member may angulate so that the height of the elongated member relative to the second bone fastener is variable. Allowing the height of the elongated member relative to the second bone fastener to vary may allow for the use of a straight elongated member with a dynamic interbody device.

Figure 20:
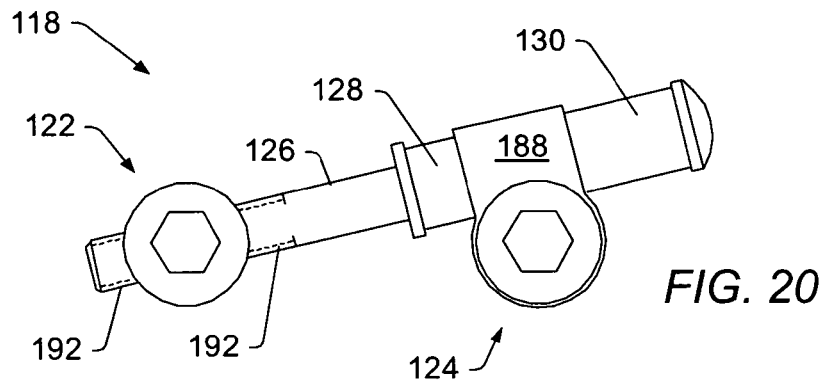
FIG. 20 depicts top view representation of an embodiment of a dynamic posterior stabilization system.

FIG. 20 depicts a top view representation of an embodiment of dynamic posterior stabilization system 118. Dynamic posterior stabilization system 118 may include first bone fastener 122, second bone fastener 124, elongated member 126, and bias members 128, 130. Elongated member 126 may include threaded portion 192. Second bone fastener 124 may include member 188. Member 188 may allow elongated member 126 to be positioned lateral to the fastener of second bone fastener 124. Lateral placement of the elongated member may allow for the establishment of multi-level stabilization systems. The elongated member of a second dynamic posterior stabilization system may couple to the collar of the second bone fastener of the first dynamic posterior stabilization system. In some embodiments, the member may position the elongated member through the collar of the second bone fastener.

Figure 21:
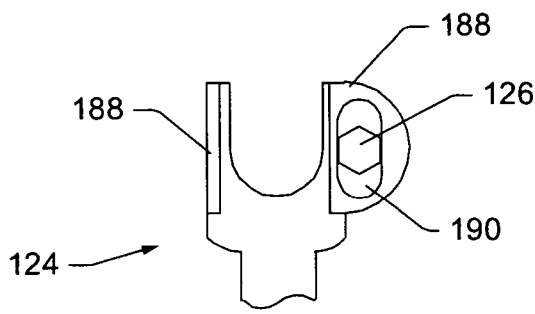
FIG. 21 depicts a front view representation of a portion of an embodiment of a second bone fastener of a dynamic posterior stabilization system.

FIG. 21 depicts a front view representation of a portion of second bone fastener 124. Member 188 may include slot. Slot 190 may allow for change in vertical position of elongated member 126 relative to second bone fastener 124. Change in vertical position of elongated member 126, relative to second bone fastener 124, along with the compression of one the bias members, may allow the dynamic posterior stabilization system to accommodate flexion or extension of vertebrae coupled to the dynamic posterior stabilization system.

The portion of elongated member 126 positioned in slot 190 may have one or more flats. For example, elongated member 126 may have a hexagonal portion. The flats may interact with member 188 to inhibit rotation of elongated member 126 relative to second bone fastener 124 while still allowing for changes in vertical position of the elongated member relative to the second bone fastener. Elongated member 126 may be able to rotate relative to the first bone fastener so that the dynamic posterior stabilization system is able to accommodate axial rotation of a first vertebra coupled to the first bone fastener relative to a second vertebra coupled to the second bone fastener.

Figure 22:
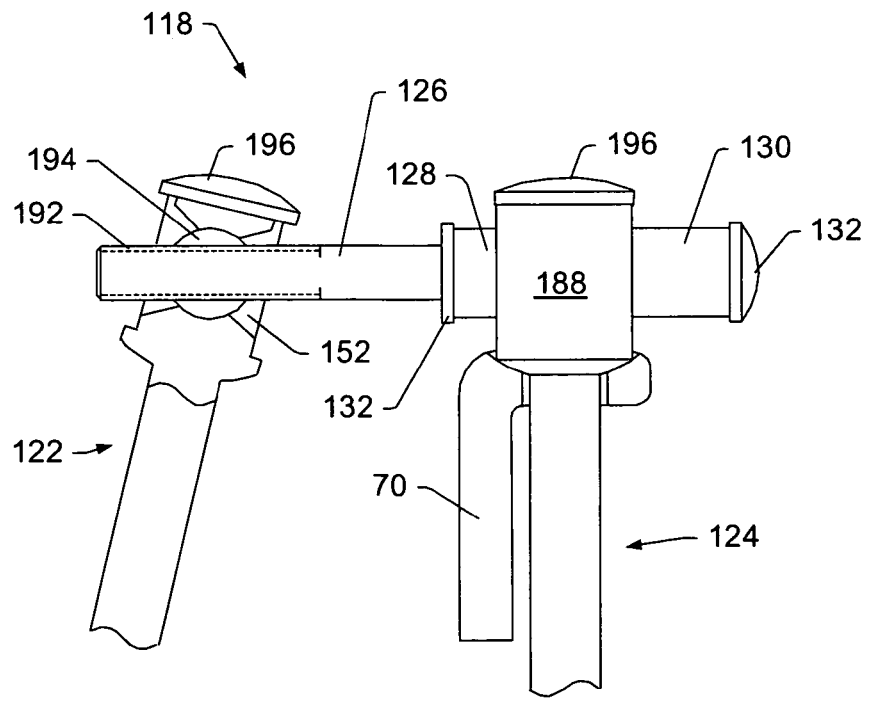
FIG. 22 depicts a side view representation of a portion of an embodiment of a dynamic posterior stabilization system with a bridge, wherein a portion of the first bone fastener is depicted in cutaway to emphasize the interior of the first bone fastener.

FIG. 22 depicts a side view representation of a portion of dynamic posterior stabilization system 148 with a portion of first bone fastener 122 depicted in cutaway to emphasize the interior of the first bone fastener. Ball 194 may be threaded on threaded portion 192 of elongated member 126. Ball 194 may be positioned in collar 152 of first bone fastener 122. Ball 194 may allow elongated member 126 to be pivotably coupled to first bone fastener 122. Closure member 196 for first bone fastener 122 may include a spherically shaped portion that complements a portion of the outer surface of ball 194. In some embodiments, the collar of the second bone fastener may accept a closure member that is identical to closure member 196 for first bone fastener 122 to avoid the need for different types of closure members for the first bone fastener and the second bone fastener.

In some embodiments, one or more lock rings may be placed on the threaded end of the elongated member. After the position of the ball is adjusted so that the elongated member will fit in the first bone fastener and the second bone fastener, one or more lock rings may be positioned against the ball to inhibit rotation of the ball relative to the elongated member. In some embodiments, an adhesive may be used to inhibit change in position of the ball relative to the elongated member after the position of the ball is set. Other systems may also be used to inhibit change in position of the ball relative to the elongated member after the position of the ball is set. In some embodiments, a portion of the end of the elongated member may be removed after the position of the ball is set so that there is little or no extension of the end of the elongated member beyond the collar of the first bone fastener when the dynamic posterior stabilization system is assembled.

In some embodiments, the ball may be at a fixed position on the elongated member. The length of the elongated member may be adjustable to allow the elongated member to be positioned in the first bone fastener and the second bone fastener. In an embodiment, a first portion of the elongated member may move relative to a second portion of the elongated member. A setscrew or other fastener may fix the position of the first portion relative to the second portion. Having a fixed position of the ball allows little or no extension of the end of the elongated member beyond the collar of the first bone fastener.

When closure member 196 is secured to collar 152 of first bone fastener 122, the closure member and the collar may allow rotation of ball 194 relative to the first bone fastener. Rotation of ball 194 allows for rotation and/or angulation of elongated member 126 relative to first bone fastener 122.

Closure member 196, collar 152 and ball 194 may allow for angulation of elongated member 126 relative to first bone fastener 122. The angular movement of elongated member 126, along with compression of bias member 128 or bias member 130, allows dynamic posterior stabilization system 118 to accommodate flexion/extension and/or lateral bending of the vertebrae coupled to the dynamic posterior stabilization system.

Elongated member assemblies may be provided in the instrument kit for the spinal stabilization procedure. The elongated member assemblies may include elongated member 126; ball 194 threaded on the elongated member; member 188; bias members 128, 130; and stops 132. During an installation procedure, the fastener of the first bone fastener 122 and the fastener of second bone fastener 124 may be positioned in the vertebrae to be stabilized. Bridge 70 may be positioned between the collar of second bone fastener 124 and the vertebra to which the second bone fastener is attached. Bridge 70 may be secured to the vertebra by the collar of the second bone fastener.

The position of ball 194 on elongated member 126 may be adjusted by rotating the ball relative to the elongated member until the position of the ball on the elongated member allows the ball to be positioned in collar 152 of first bone fastener 122 when member 188 is positioned in the collar of second bone fastener 124. Member 188 may be coupled to the collar of the second bone fastener and ball 194 may be positioned in collar 152 of first bone fastener 122. Closure member 196 may be used to secure member 188 to second bone fastener 124. Closure member 196 may be used to couple ball 194 to collar 152 of first bone fastener 122.

In some dynamic posterior stabilization system embodiments, the passage through the second bone fastener for the elongated member may inhibit rotation of the elongated member and may also inhibit angulation of the elongated member relative to the second bone fastener. The second bone fastener may be configured to move axially relative to the elongated member when the second bone fastener is coupled to a vertebra. The first bone fastener may inhibit axial movement of the elongated member relative to the first bone fastener, but the first bone fastener may allow for rotation of the elongated member relative to the first bone fastener. At least a portion of the elongated member may be curved so that the assembled dynamic posterior stabilization system allows for flexion/extension and/or lateral bending of vertebrae coupled to the dynamic posterior stabilization system. The ability of the elongated member to rotate relative to the first bone fastener but not the second bone fastener may allow for accommodation of axial rotation movement of vertebrae coupled to the dynamic posterior stabilization system.

Figure 23:
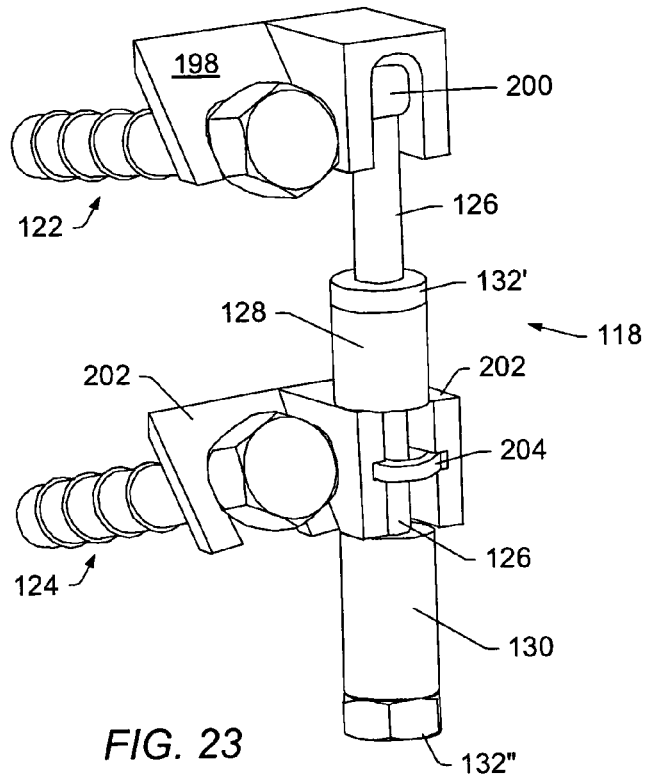
FIG. 23 depicts a perspective view of an embodiment of a dynamic posterior stabilization system.

FIG. 23 depicts an alternate embodiment of a dynamic posterior stabilization system that allows elongated member to angulate so that the height of the elongated member relative to the second bone fastener is variable. Dynamic posterior stabilization system 118 may include first bone fastener 122, second bone fastener 124, elongated member 126, and bias members 128, 130. Elongated member may be coupled to collar 198 of first bone fastener 122 so that rotation of the elongated member relative to the first bone fastener about a central axis of the elongated member is inhibited. When elongated member 126 is positioned in collar 198, the elongated member may angulate so that a height of the elongated member relative to second bone fastener 124 is variable.

Figure 24:
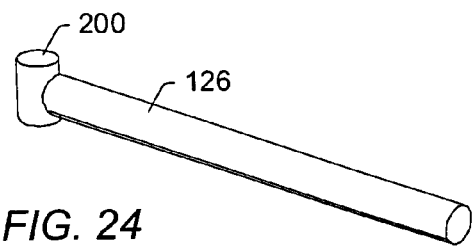
FIG. 24 depicts a perspective view of the elongated member of the dynamic posterior stabilization system depicted in FIG. 23.
Figure 25:
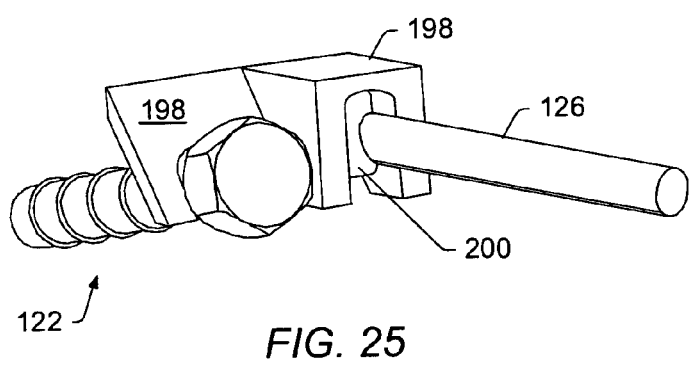
FIG. 25 depicts the first bone fastener of the dynamic posterior stabilization system after insertion of the elongated member.

FIG. 24 depicts a perspective view of an embodiment of elongated member 126. Elongated member may include end portion 200. End portion 200 may fit in a keyway in the collar of the first bone fastener to inhibit removal of the elongated member from the collar. When end portion 200 is positioned in the keyway, rotation of the rotation of elongated member 126 about the longitudinal axis of the elongated member is inhibited, but the elongated member may be angulated relative to the first bone fastener. FIG. 25 depicts elongated member 126 after insertion into collar 198 of first bone fastener 122. After insertion, elongated member may be rotated about the longitudinal axis of the elongated member to seat end portion 200 in the keyway of collar 198.

FIG. 23 depicts dynamic posterior stabilization system after elongated member 126 is angulated downward to position a portion of the elongated member in collar 202 of second bone fastener 124. When the portion of elongated member 126 is positioned in collar 202 of second bone fastener 124, stop 204 may be coupled to the collar. Stop 204 may inhibit removal of elongated member from collar 202. Bias member 128 may be positioned against collar 202, and stop 132' may be used to fix the position of the bias member. Bias member 130 may be positioned on elongated member 126 and stop 132" may be used to inhibit removal of the bias member from the elongated member.

Figure 26:
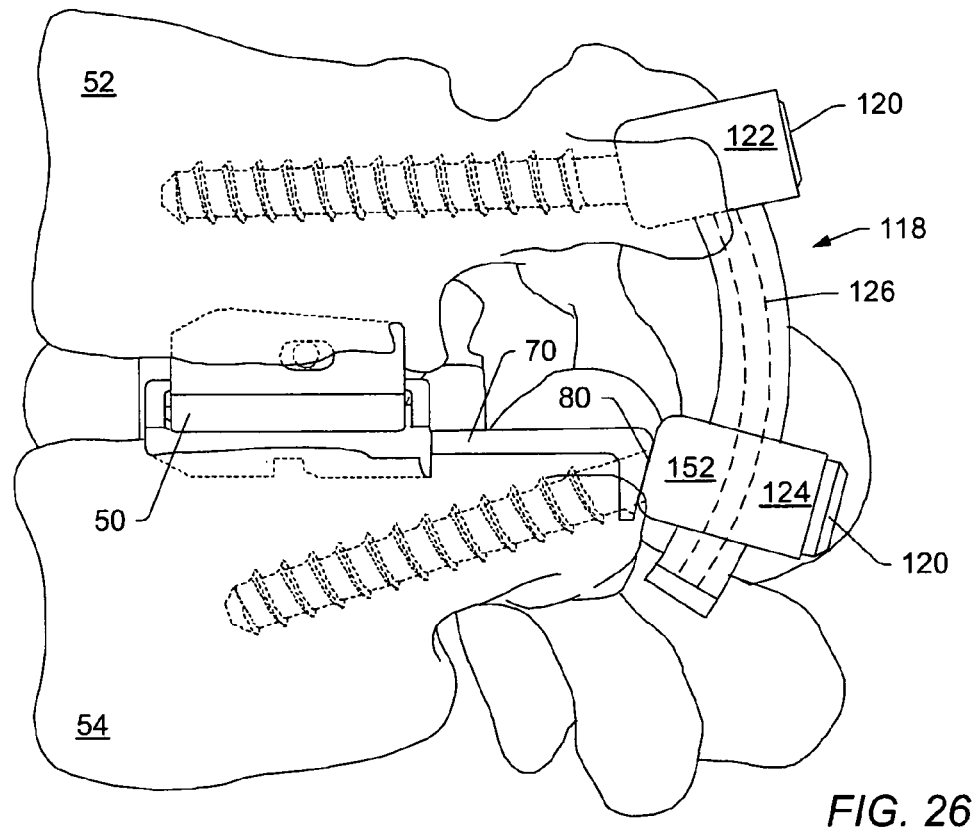
FIG. 26 depicts a representation of a dynamic interbody device and a posterior stabilization system coupled to vertebrae.

FIG. 26 depicts a representation of dynamic interbody device 50 and posterior stabilization system 118 positioned between vertebrae 52, 54. Bridge 70 of dynamic interbody device 50 may be coupled to second bone fastener 124 of dynamic posterior stabilization system 118. Coupling dynamic interbody device 50 to dynamic posterior stabilization system 118 may inhibit undesired migration of the dynamic interbody device relative to vertebrae 52, 54 while still allowing for flexion, extension, lateral bending, and/or axial rotation of the vertebrae.

When closure member 120 is tightened in collar 152 of second bone fastener 124, a bottom surface of the collar may align and be tightened against angled surface 80 of bridge 70. Tightening closure member 120 may fix the position of bridge 70. When closure member 120 is tightened so that the bottom of collar 152 is positioned against angled surface 80, the center of curvature of elongated member 126 may align or substantially align with the center or centers of curvature of dynamic interbody device 50 that allow for flexion/extension and/or lateral bending. Aligning or substantially aligning the center of curvature of elongated member 126 with the center or centers of curvature of dynamic interbody device 50 allows the elongated member to move relative to second bone fastener 124 during flexion/extension and/or lateral bending so that dynamic posterior stabilization system 118 works in conjunction with the dynamic interbody device.

Dynamic posterior stabilization system 118 may share a portion of the load applied to the vertebrae 52, 54 while providing guidance and resistance to flexion/extension and/or lateral bending that is, or is approximate to, the resistance provided by a normal functional spinal unit. Allowing for movement of the dynamic interbody device and for movement of the dynamic posterior stabilization system may inhibit deterioration of adjacent functional spinal units.

In some embodiments, first bone fastener 122 of dynamic posterior stabilization system is placed in the more cephalad of the vertebrae to be stabilized. Bridge 70 may couple dynamic interbody device 50 to dynamic posterior stabilization system 118. Bridge may be coupled to dynamic posterior stabilization system 118 at or near to second bone fastener 124. Coupling bridge 70 to dynamic posterior stabilization system 118 at or near to second bone fastener 124 may inhibit or eliminate contact of the bridge with nerves extending from between the vertebrae.

Figure 27:
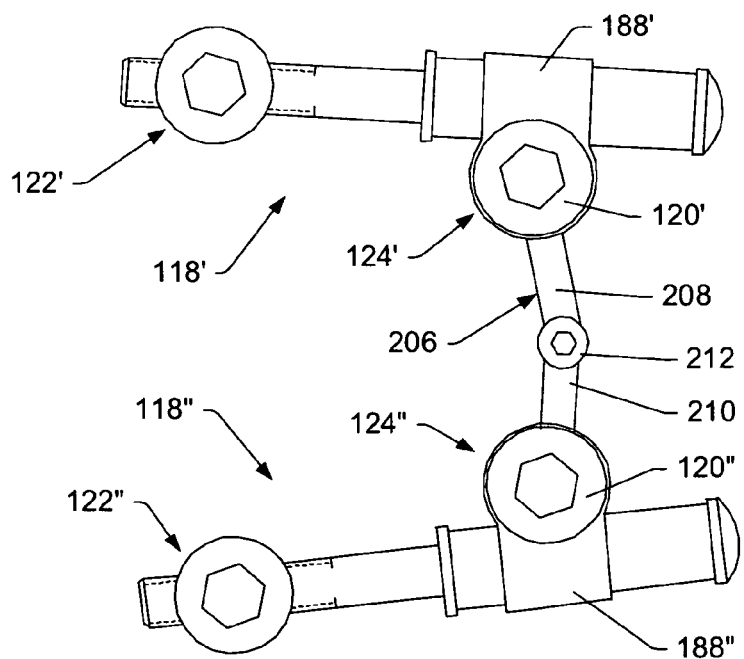
FIG. 27 depicts a representation of a transverse connector that couples a first dynamic posterior stabilization system to a second dynamic posterior stabilization system.

In some embodiments, a first dynamic posterior stabilization system coupled to vertebrae may be unconnected to a second dynamic posterior stabilization system on a contralateral side of the vertebrae. In some embodiments, one or more transverse connectors may connect dynamic posterior stabilization systems placed on contralateral sides of vertebrae. FIG. 27 depicts a schematic representation of transverse connector 206 coupled to dynamic posterior stabilization systems 118', 118". Transverse connector 206 may be coupled to the collars of second bone fasteners 124', 124". Transverse connector 206 may include first arm 208, second arm 210, and joint 212. To attach transverse connector 206, a fastener of joint 212 may be loosened. First arm 208 may be positioned in the collar of second bone fastener 124'. Second arm 210 may be positioned in the collar of second bone fastener 124". Closure member 120; may secure member 188' and first arm 208 to second bone fastener 124'. Closure member 120" may secure member 188" and second arm 210 to second bone fastener 124". The fastener of joint 212 may be tightened. Transverse connector may join dynamic posterior stabilization system 118' to dynamic posterior stabilization system 118" and increase the stiffness of the stabilization system. Attaching transverse connector 206 to the collars of second bone fasteners 124', 124" does not inhibit movement of elongated members 126', 126" relative to first bone fasteners 122', 122" and/or the second bone fasteners, In some embodiments, a single dynamic interbody device may be positioned in a disc space between vertebrae. The dynamic interbody device may be positioned using an anterior, posterior, anterio-lateral, or other approach. A bridge may couple the dynamic interbody device to a dynamic posterior stabilization system. In some embodiments, a separate component bridge is coupled to the dynamic posterior stabilization system to inhibit posterior migration of the dynamic interbody device.

In some embodiments, a posterior approach may be used to install a stabilization system for a patient. The stabilization system may replace one or more parts of a functional spinal unit of the patient. The stabilization system may include one or more dynamic interbody devices, and one or more dynamic posterior stabilization systems.

During a posterior insertion procedure of a spinal stabilization system, a fast dynamic interbody device may be installed on a first side of the patient, and then a second dynamic interbody device may be installed on a second side (contralateral side) of the patient. The dynamic interbody devices may be bimodal devices. A facet joint between the pair of vertebrae to be stabilized may be removed on the first side to provide access to the intervertebral disc between the vertebrae. Tissue may be retracted to provide access to the intervertebral disc between the vertebrae. A discectomy may be performed to remove all or a portion of the intervertebral disc. A channel may be formed in one or both of the vertebrae for the dynamic interbody device or for a keel of the dynamic interbody device. The dynamic interbody device may be installed in the formed space between the vertebrae.

In some embodiments, a bone fastener may be secured to each of the vertebrae to be stabilized. The bone fasteners may be used during insertion of the dynamic interbody device to provide distraction of the vertebrae. The bone fasteners may be components of a dynamic posterior stabilization system. In some embodiments, a bridge coupled to the dynamic interbody device may be coupled to one of the bone fasteners secured to the vertebrae.

After the dynamic interbody device on the first side is inserted between the vertebrae, the dynamic posterior stabilization system may be formed. After insertion of the bone fasteners in the vertebrae, the elongated member and bias member may be coupled to the bone fasteners.

A second dynamic interbody device may be installed on the contralateral side of the patient. In some embodiments, a transverse connector may be couple the dynamic posterior stabilization system on the first side to the dynamic posterior stabilization system on the second side.

Figure 28:
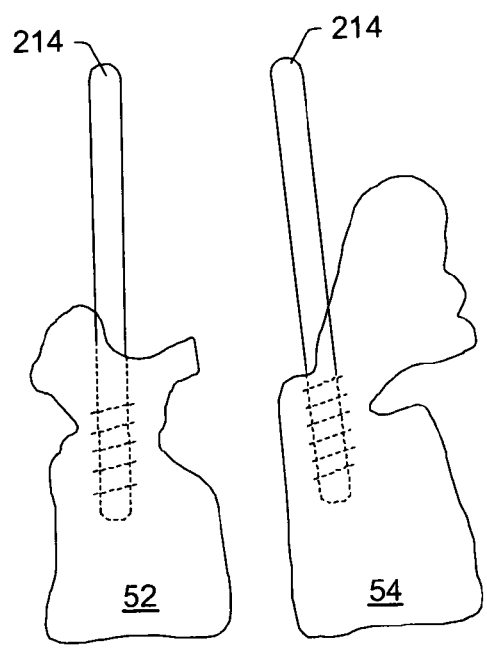
FIG. 28 depicts a representation of pins placed in vertebrae to be stabilized.

During some spinal stabilization procedures, posterior elements of the vertebrae to be stabilized may be removed. Pins may be threaded in the vertebrae. The pins may be inserted parallel or inclined away from the endplates of the vertebrae to be stabilized. A discectomy may be performed to remove the intervertebral disc. The pins may be used to inhibit compression of the disc space between the vertebrae. FIG. 28 depicts pins 214 positioned in vertebrae 52, 54 on a first side of the patient. Pins may also be positioned in vertebrae 52, 54 on the second side of the patient.

Figure 29:
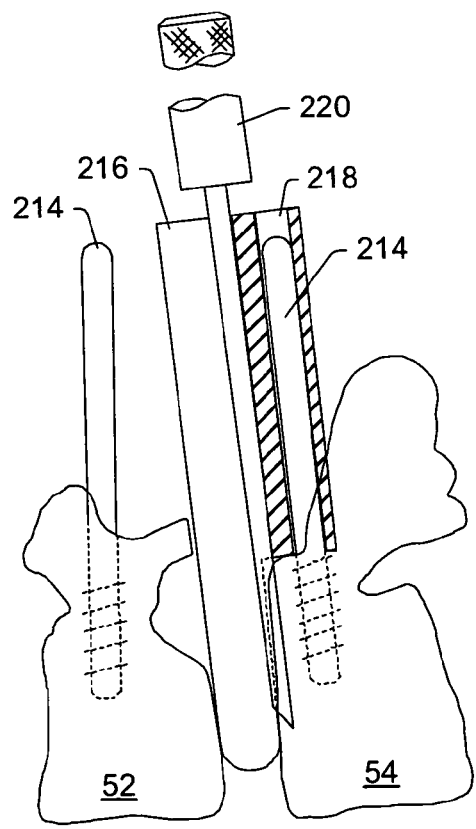
FIG. 29 depicts a representation of a distractor plug and a keel cutter during a spinal stabilization procedure.

Pins 214 may be used to distract the disc space between vertebrae 52, 54. In some embodiments, a distraction plug may be inserted in the disc space of the second side to hold the disc space open. A guide of a keel cutter may be placed over a pin. A head of the keel cutter may be impacted to form a channel in a surface of one of the vertebra. FIG. 29 depicts distraction plug 216 positioned in the disc space between vertebrae 52, 54. Guide 218 of keel cutter 220 is positioned over pin 214, and the keel cutter has been used to form a channel for a dynamic interbody implant in vertebra 54. After the channel has been formed, keel cutter may be removed from pin 214. The endplates of vertebrae 52, 54 may be prepared for the dynamic interbody implant by removing any osteophytes and/or tissue. A distraction plug 216 may be inserted in the first side, and distraction plug 216 may be removed from the second side. The keel cutter may be placed over the appropriate pin on the second side. The keel cutter may be used to form a channel in the vertebra on the second side. The vertebrae on the second side may be prepared for receiving a dynamic interbody device. After the first side and second side are prepared, the distraction plug may be removed. The height of the disc space may be maintained by force applied to pins 214.

Figure 30:
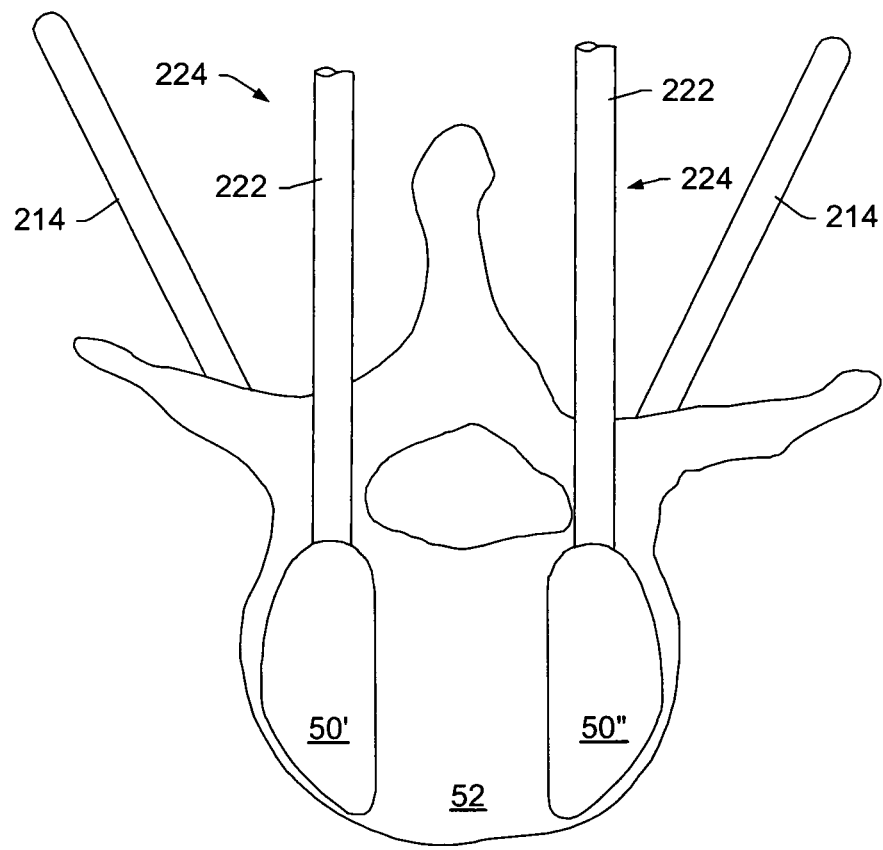
FIG. 30 depicts a representation of dynamic interbody devices inserted in a disc space between vertebrae.

Trial implants may be used to determine the heights of the dynamic interbody devices to be inserted into the prepared disc space. Appropriate dynamic interbody devices may be attached to inserters. The dynamic interbody devices may be inserted into the prepared disc space. The dynamic interbody devices may be inserted into the disc space and rotated to place keels of the dynamic interbody devices in the channels formed in vertebra. FIG. 30 depicts a representation of dynamic interbody devices 50', 50" inserted in the disc space. Shafts 222 of the inserters 224 should be parallel to each other and dynamic interbody devices 50', 50" should be inserted to the same depth in the disc space. After insertion, the distraction force is removed and the spine is allowed to return to a neutral position. If necessary, pins 214 may be used to compress the vertebrae towards each other. Inserters 224 may be removed from the dynamic interbody devices.

Figure 31:
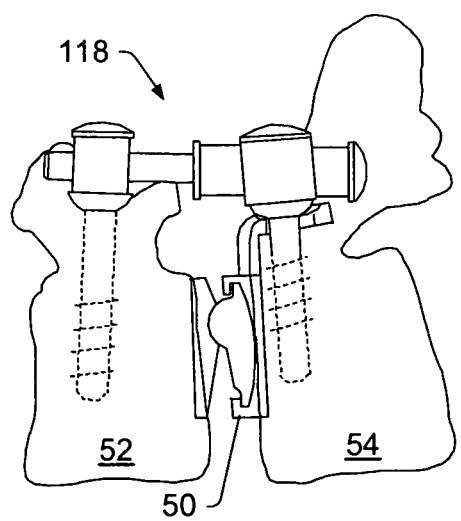
FIG. 31 depicts a representation of an embodiment of a dynamic interbody device and an embodiment of a dynamic posterior stabilization system of a spinal stabilization system.

Pins 214 may be removed from the vertebrae. Fasteners of a dynamic posterior stabilization system may be inserted into the openings in the vertebra where the pins were located. In some embodiments, a bridge may be coupled to the second bone fastener of the dynamic posterior stabilization system. Ball 194 (depicted in FIG. 22) on elongated member 126 may be positioned on the elongated member so that member 188 couples to the second bone fastener when the ball is positioned in the first bone fastener. When ball is positioned in the first bone fastener and member 188 is coupled to the second bone fastener, closure members may be secured to the collars of the first bone fastener and the second bone fastener to complete the dynamic posterior stabilization system. A dynamic posterior stabilization system may be formed on each side of the patient. FIG. 31 depicts dynamic interbody device 50 and dynamic posterior stabilization system 118 coupled to vertebrae 52, 54.

In some embodiments, a dynamic interbody device may be installed between a pair of vertebrae using an anterior approach. After insertion of the dynamic interbody device, a dynamic posterior stabilization system can be attached to the vertebrae. In some embodiments, a bridge is coupled to the dynamic posterior stabilization system. In some embodiments, the bridge is coupled to both the dynamic interbody device and the dynamic posterior stabilization system.

In this patent, certain U.S. patents, and U.S. patent applications have been incorporated by reference. The text of such U.S. patents and U.S. patent applications is, however, only incorporated by reference to the extent that no conflict exists between such text and the other statements and drawings set forth herein. In the event of such conflict, then any such conflicting text in such incorporated by reference U.S. patents and U.S. patent applications is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A stabilization system for a human spine, comprising:
   a dynamic interbody device positioned in a disc space between a first vertebra and a second vertebra during use, wherein the dynamic interbody device rotates about a center of rotation during use to facilitate movement of the first vertebra relative to the second vertebra during use; and
   a posterior stabilization system comprising:
      a first bone fastener configured to couple to a posterior of the first vertebra during use;
      a second bone fastener configured to couple to a posterior of the second vertebra during use;
      a rigid elongated member coupled to the first bone fastener and the second bone fastener during use, wherein the rigid elongated member is arched along at least a portion of its length about a center of curvature to form an arched portion of the rigid elongated member, and wherein the center of curvature of the rigid elongated member substantially aligns with the center of interbody device during use; and
   a flexible bias member configured to couple to the rigid elongated member, wherein the bias member is configured to provide resistance to movement of the second bone fastener relative to the first bone fastener when the first bone fastener and the second bone fastener are coupled to the first vertebrae and second vertebrae respectively during use.

2. The stabilization system for a human spine of claim 1, wherein the second bone fastener comprises an aperture extending there through, and wherein at least a portion of the arched portion of the rigid elongated member is configured to slide longitudinally through the aperture during use.

3. The stabilization system for a human spine of claim 2, wherein the rigid elongated member is fixedly coupled to the first bone fastener to substantially inhibit longitudinal movement of the elongated member relative to the first bone fastener.

4. The stabilization system for a human spine of claim 1, wherein a first side of an arched portion of the elongated member comprises a concave curvature about the center of curvature.

5. The stabilization system for a human spine of claim 4, wherein a second side of an arched portion of the elongated member substantially opposite the first side comprises a convex curvature about the center of curvature, and wherein the first side is configured to substantially face toward the human spine during use.

6. The stabilization system for a human spine of claim 1, further comprising a bridge configured to fix a position of the at least one dynamic interbody device relative to the posterior stabilization system during use such that the center of rotation of the dynamic interbody device substantially aligns with the center of curvature of the arched portion of the rigid elongated member during use.

7. The stabilization system for a human spine of claim 6, wherein the bridge comprises a rigid member configured to couple to at least a portion of the posterior stabilization system and configured to couple to the dynamic interbody device during use.

8. The stabilization system for a human spine of claim 7, wherein the bridge is configured to couple to the first or second bone fastener and the dynamic interbody device during use.

9. The stabilization system for a human spine of claim 6, wherein the bridge is configured to inhibit migration of the dynamic interbody device from the disc space between the first vertebra and the second vertebra during use.

10. The stabilization system for a human spine of claim 6, wherein the bridge is an integral member of the dynamic interbody device.

11. A stabilization system for a human spine, comprising:
    a dynamic interbody device positioned in a disc space between a first vertebra and a second vertebra during use, wherein the dynamic interbody device pivots about a center of rotation during use to facilitate flexion and extension movement of the first vertebra relative to the second vertebra during use; and
    a posterior stabilization system comprising:
       a first bone fastener coupled to a posterior of the first vertebra during use;
       a second bone fastener configured to couple to a posterior of the second vertebra during use;
       a rigid elongated member coupled to the first bone fastener and the second bone fastener during use, wherein the rigid elongated member comprises a curved longitudinal axis that is arched along at least a portion of its length about a center of curvature to form an arched portion of the rigid elongated member, and wherein the center of curvature of the curved longitudinal axis substantially aligns with the center of rotation of the dynamic the center of rotation of the dynamic interbody device during use; and
    a flexible bias member configured to couple to the rigid elongated member, wherein the bias member is configured to provide resistance to movement of the second bone fastener relative to the first bone fastener when the first bone fastener and the second bone fastener are coupled to the first vertebrae and second vertebrae respectively during use.

12. The stabilization system for a human spine of claim 11, wherein the second bone fastener comprises an aperture extending there through, and wherein at least a portion of the arched portion of the rigid elongated member is configured to slide longitudinally through the aperture during use.

13. The stabilization system for a human spine of claim 12, wherein the rigid elongated member is fixedly coupled to the first bone fastener to substantially inhibit longitudinal movement of the elongated member relative to the first bone fastener.

14. The stabilization system for a human spine of claim 11, wherein a first side of an arched portion of the elongated member comprises a concave curvature about the center of curvature.

15. The stabilization system for a human spine of claim 14, wherein a second side of an arched portion of the elongated member substantially opposite the first side comprises a convex curvature about the center of curvature, and wherein the first side is configured to substantially face toward the human spine during use.

16. The stabilization system for a human spine of claim 11, further comprising a bridge configured to fix a position of the at least one dynamic interbody device relative to the posterior stabilization system during use such that the center of rotation of the dynamic interbody device substantially aligns with the center of curvature of the arched portion of the rigid elongated member during use.

17. The stabilization system for a human spine of claim 16, wherein the bridge comprises a rigid member configured to couple to at least a portion of the posterior stabilization system and configured to couple to the dynamic interbody device during use.

18. The stabilization system for a human spine of claim 17, wherein the bridge is configured to couple to the first or second bone fastener and the dynamic interbody device during use.

19. The stabilization system for a human spine of claim 16, wherein the bridge is configured to inhibit migration of the dynamic interbody device from the disc space between the first vertebra and the second vertebra during use.

20. The stabilization system for a human spine of claim 16, wherein the bridge is an integral member of the dynamic interbody device.

21. A stabilization system for a human spine, comprising:
a dynamic interbody device positioned in a disc space between a first vertebra and a second vertebra during use, wherein the dynamic interbody device pivots about a rotational axis during use to facilitate flexion and extension movement of the first vertebra relative to the second vertebra about the rotational axis during use; and
a posterior stabilization system comprising:
a first bone fastener coupled to the first vertebra during use;
a second bone fastener coupled to the second vertebra during use;
a rigid elongated member coupled to the first bone fastener and the second bone fastener during use, wherein the rigid elongated member comprises a curved longitudinal axis that is arched along at least a portion of its length about a center of curvature, and wherein the center of curvature of the curved longitudinal axis substantially aligns with the rotational axis of the during use; and
a flexible bias member configured to couple to the rigid elongated member, wherein the bias member is configured to provide resistance to movement of the second bone fastener relative to the first bone fastener when the first bone fastener and the second bone fastener are coupled to the first vertebrae and second vertebrae respectively during use.

22. The stabilization system for a human spine of claim 21, wherein the second bone fastener comprises an aperture extending there through, and wherein an arched portion of the rigid elongated member is configured to slide longitudinally through the aperture during use.

23. The stabilization system for a human spine of claim 22, wherein the rigid elongated member is fixedly coupled to the first bone fastener to substantially inhibit longitudinal movement of the elongated member relative to the first bone fastener.

24. The stabilization system for a human spine of claim 21, wherein a first side of an arched portion of the elongated member comprises a concave curvature about the center of curvature.

25. The stabilization system for a human spine of claim 24, wherein a second side of an arched portion of the elongated member substantially opposite the first side comprises a convex curvature about the center of curvature, and wherein the first side is configured to substantially face toward the human spine during use.

26. The stabilization system for a human spine of claim 21, further comprising a bridge configured to fix a position of the at least one dynamic interbody device relative to the posterior stabilization system such that the center of rotation of the dynamic interbody device substantially aligns with the center of curvature of the arched portion of the rigid elongated member during use.

27. The stabilization system for a human spine of claim 26, wherein the bridge comprises a rigid member configured to couple to at least a portion of the posterior stabilization system and configured to couple to the dynamic interbody device during use.

28. The stabilization system for a human spine of claim 27, wherein the bridge is configured to couple to the first or second bone fastener and the dynamic interbody device during use.

29. The stabilization system for a human spine of claim 26, wherein the bridge is configured to inhibit migration of the dynamic interbody device from the disc space between the first vertebra and the second vertebra during use.

30. The stabilization system for a human spine of claim 26, wherein the bridge is an integral member of the dynamic interbody device.

* * * * *

UNITED STATES PATENT AND TRADEMARK OFFICE
CERTIFICATE OF CORRECTION

| | | |
|---|---|---|
| PATENT NO. | : 8,603,168 B2 | Page 1 of 1 |
| APPLICATION NO. | : 11/371376 | |
| DATED | : December 10, 2013 | |
| INVENTOR(S) | : Gordon et al. | |

It is certified that error appears in the above-identified patent and that said Letters Patent is hereby corrected as shown below:

In the Claims:

Claim 1, col. 25, line 49, please delete "center of interbody device" and substitute therefor --center of rotation of the dynamic interbody device--.

Claim 11, col. 26, line 54, please delete "of rotation of the dynamic the center of rotation of the interbody device during use" and substitute therefor --of rotation of the dynamic interbody device during use--.

Claim 21, col. 28, line 3, please delete "axis of the during use" and substitute therefor --axis of the dynamic interbody device during use--.

Signed and Sealed this
Fifteenth Day of April, 2014

Michelle K. Lee
*Deputy Director of the United States Patent and Trademark Office*